(12) United States Patent
Stearns et al.

(10) Patent No.: US 10,369,303 B2
(45) Date of Patent: Aug. 6, 2019

(54) TROCAR ASSEMBLY WITH PNEUMATIC SEALING

(71) Applicant: SurgiQuest, Inc., Milford, CT (US)

(72) Inventors: Ralph Stearns, Bozrah, CT (US); Jack B. Stubbs, Waynesville, OH (US)

(73) Assignee: Conmed Corporation, Utica, NY (US)

( * ) Notice: Subject to any disclaimer, the term of this patent is extended or adjusted under 35 U.S.C. 154(b) by 178 days.

(21) Appl. No.: 14/196,176

(22) Filed: Mar. 4, 2014

(65) Prior Publication Data

US 2014/0188038 A1     Jul. 3, 2014

Related U.S. Application Data

(60) Continuation of application No. 12/950,684, filed on Nov. 19, 2010, now abandoned, which is a division of
(Continued)

(51) Int. Cl.
*A61M 13/00*     (2006.01)
*A61B 17/34*     (2006.01)
(Continued)

(52) U.S. Cl.
CPC ....... *A61M 13/003* (2013.01); *A61B 17/3421* (2013.01); *A61B 17/3423* (2013.01);
(Continued)

(58) Field of Classification Search
CPC .......... A61M 13/00; A61M 2202/0225; A61M 2205/3344; A61M 2202/02;
(Continued)

(56) References Cited

U.S. PATENT DOCUMENTS 1,926,608 A  *  9/1933  Ziegler ............... A61M 3/0279
                                                        604/249
3,224,320 A     12/1965  Knudsen
(Continued)

FOREIGN PATENT DOCUMENTS

DE     2538758 A1     3/1977
DE     2847561 A1     5/1980
(Continued)

OTHER PUBLICATIONS

International Search Report and Written Opinion for PCT/US2012/28065, dated Aug. 28, 2012.
(Continued)

*Primary Examiner* — Bhisma Mehta
*Assistant Examiner* — Laura C Schell
(74) *Attorney, Agent, or Firm* — Locke Lord LLP; Scott D. Wofsy

(57) ABSTRACT

A trocar for use in a minimally invasive surgical procedure includes an elongated body, nozzle means and means for delivering a pressurized flow of fluid to the nozzle means. The elongated body has a generally tubular configuration with coaxially arranged inner and outer walls and longitudinally opposed proximal and distal end portions, with the inner wall defining a lumen to accommodate passage of an instrument therethrough. The nozzle means is operatively associated with the inner wall of the body for directing pressurized fluid into the lumen to develop a pressure differential in an area within a region extending from a location adjacent a distal end portion of the lumen to a location adjacent a proximal end portion of the lumen, to form a fluid seal around an instrument passing therethrough.

1 Claim, 24 Drawing Sheets

Related U.S. Application Data application No. 11/517,929, filed on Sep. 8, 2006, now Pat. No. 7,854,724, which is a continuation-in-part of application No. 10/776,923, filed on Feb. 11, 2004, now Pat. No. 7,338,473, which is a continuation-in-part of application No. 10/739,872, filed on Dec. 18, 2003, now Pat. No. 7,285,112, which is a continuation-in-part of application No. 10/441,149, filed on May 17, 2003, now Pat. No. 7,182,752.

(60) Provisional application No. 60/461,149, filed on Apr. 8, 2003.

(51) Int. Cl.
*A61M 1/28* (2006.01)
*A61B 17/00* (2006.01)
*A61B 90/00* (2016.01)

(52) U.S. Cl.
CPC ...... *A61B 17/3462* (2013.01); *A61B 17/3474* (2013.01); *A61B 17/3498* (2013.01); *A61M 1/28* (2013.01); *A61M 13/006* (2014.02); *A61B 2017/00265* (2013.01); *A61B 2090/064* (2016.02); *A61M 2202/0225* (2013.01); *A61M 2205/3344* (2013.01)

(58) Field of Classification Search
CPC .. A61M 2205/3331; A61M 2210/1021; A61M 2005/006; A61M 2210/1017; A61M 13/003; A61M 13/006; A61M 2005/3201; A61M 5/3297; A61M 2025/0004; A61M 2025/0006; A61M 2025/0073; A61M 2205/14; A61M 2206/18; A61M 2206/20; A61M 1/28; A61F 9/00736–00763; A61B 17/3474; A61B 17/3421; A61B 17/3423; A61B 17/3462; A61B 17/3498
USPC ..................................... 604/23–26
See application file for complete search history.

(56) References Cited

U.S. PATENT DOCUMENTS

| | | |
|---|---|---|
| 3,357,433 A | 12/1967 | Fourestier et al. |
| 3,459,189 A | 8/1969 | Alley et al. |
| 3,556,085 A | 1/1971 | Takahashi |
| 4,184,510 A | 1/1980 | Murry et al. |
| 4,191,191 A | 3/1980 | Auburn |
| 4,265,572 A | 5/1981 | Bourdois et al. |
| 4,319,563 A | 3/1982 | Kubota |
| 4,535,773 A | 8/1985 | Yoon |
| 4,735,603 A | 4/1988 | Goodson et al. |
| 4,792,335 A | 12/1988 | Goosen et al. |
| 4,869,717 A | 9/1989 | Adair |
| 5,013,294 A | 5/1991 | Baier |
| 5,057,082 A | 10/1991 | Burchette, Jr. |
| 5,058,603 A | 10/1991 | Doi et al. |
| 5,066,288 A | 11/1991 | Deniega et al. |
| 5,122,122 A | 6/1992 | Allgood |
| 5,147,376 A | 9/1992 | Pianetti et al. |
| 5,159,920 A | 11/1992 | Condon et al. |
| 5,190,068 A | 3/1993 | Philbin |
| 5,199,944 A | 4/1993 | Cosmescu |
| 5,203,767 A | 4/1993 | Cloyd |
| 5,256,149 A | 10/1993 | Banik et al. |
| 5,271,380 A | 12/1993 | Riek et al. |
| 5,284,473 A | 2/1994 | Calabria |
| 5,290,276 A | 3/1994 | Sewell, Jr. |
| 5,300,047 A * | 4/1994 | Beurrier ............... A61B 17/34 137/487.5 |
| 5,312,351 A | 5/1994 | Gerrone |
| 5,328,458 A | 7/1994 | Sekino et al. |
| 5,330,437 A | 7/1994 | Durman |
| 5,334,150 A | 8/1994 | Kaali |
| 5,342,383 A | 8/1994 | Thomas |
| 5,376,076 A | 12/1994 | Kaali |
| 5,380,291 A | 1/1995 | Kaali |
| 5,385,572 A | 1/1995 | Nobles et al. |
| 5,391,153 A | 2/1995 | Haber et al. |
| 5,405,328 A | 4/1995 | Vidal et al. |
| 5,411,474 A | 5/1995 | Ott et al. |
| 5,429,483 A | 7/1995 | Tamari |
| 5,431,151 A | 7/1995 | Riek et al. |
| 5,441,041 A | 8/1995 | Sauer et al. |
| 5,445,142 A | 8/1995 | Hassler, Jr. |
| 5,467,762 A | 11/1995 | Sauer et al. |
| 5,545,150 A | 8/1996 | Danks et al. |
| 5,551,947 A | 9/1996 | Kaali |
| 5,556,386 A | 9/1996 | Todd |
| 5,562,696 A | 10/1996 | Nobles et al. |
| 5,569,160 A | 10/1996 | Sauer et al. |
| 5,569,291 A | 10/1996 | Privitera et al. |
| 5,569,292 A | 10/1996 | Scwemberger et al. |
| 5,591,192 A | 1/1997 | Privitera et al. |
| 5,607,440 A | 3/1997 | Danks et al. |
| 5,607,441 A | 3/1997 | Sierocuk et al. |
| 5,609,562 A | 3/1997 | Kaali |
| 5,624,459 A | 4/1997 | Kortenbach et al. |
| 5,647,840 A | 7/1997 | D'Amelio et al. |
| 5,658,236 A | 8/1997 | Sauer et al. |
| 5,674,184 A | 10/1997 | Hassler, Jr. |
| 5,685,820 A | 11/1997 | Riek et al. |
| 5,690,664 A | 11/1997 | Sauer et al. |
| 5,697,913 A | 12/1997 | Sierocuk et al. |
| 5,707,382 A | 1/1998 | Sierocuk et al. |
| 5,720,761 A | 2/1998 | Kaali |
| 5,738,628 A | 4/1998 | Sierocuk et al. |
| 5,779,728 A | 7/1998 | Lunsford et al. |
| 5,797,943 A | 8/1998 | Danks et al. |
| 5,797,944 A | 8/1998 | Nobles et al. |
| 5,800,381 A | 9/1998 | Ognier |
| 5,800,451 A | 9/1998 | Buess et al. |
| 5,817,061 A | 10/1998 | Goodwin et al. |
| 5,817,062 A | 10/1998 | Flom et al. |
| 5,849,005 A | 12/1998 | Garrison et al. |
| 5,860,996 A | 1/1999 | Urban et al. |
| 5,916,198 A | 6/1999 | Dillow |
| 5,951,464 A | 9/1999 | Takahashi et al. |
| 5,964,223 A * | 10/1999 | Baran ............... A61M 16/0463 128/200.14 |
| 5,976,168 A | 11/1999 | Chin |
| 5,989,228 A | 11/1999 | Danks et al. |
| 6,007,481 A | 12/1999 | Riek et al. |
| 6,017,356 A | 1/2000 | Frederick et al. |
| 6,042,573 A | 3/2000 | Lucey |
| 6,063,099 A | 5/2000 | Danks et al. |
| 6,068,609 A * | 5/2000 | Ott et al. .................. 604/26 |
| 6,162,196 A | 12/2000 | Hart et al. |
| 6,171,493 B1 | 1/2001 | Zia et al. |
| 6,203,568 B1 | 3/2001 | Lombardi et al. |
| 6,206,823 B1 | 3/2001 | Kolata et al. |
| 6,217,555 B1 | 4/2001 | Hart et al. |
| 6,228,058 B1 | 5/2001 | Dennis et al. |
| D443,360 S | 6/2001 | Haberland |
| 6,253,766 B1 | 7/2001 | Niles et al. |
| 6,277,137 B1 | 8/2001 | Chin |
| 6,283,948 B1 | 9/2001 | McKernan et al. |
| 6,299,592 B1 | 10/2001 | Zander |
| 6,302,873 B1 | 10/2001 | Moenning |
| 6,309,382 B1 | 10/2001 | Garrison et al. |
| 6,439,541 B1 | 8/2002 | Nosel et al. |
| 6,471,638 B1 | 10/2002 | Chang et al. |
| 6,478,806 B2 | 11/2002 | McFarlane |
| 6,482,181 B1 | 11/2002 | Racenet et al. |
| 6,497,687 B1 | 12/2002 | Blanco |
| 6,508,859 B1 | 1/2003 | Zia et al. |
| 6,544,210 B1 | 4/2003 | Trudel et al. |
| 6,579,270 B2 | 6/2003 | Sussman et al. |
| 6,613,063 B1 | 9/2003 | Hunsberger |
| 6,645,197 B2 | 11/2003 | Garrison et al. |
| 6,685,630 B2 | 2/2004 | Sauer et al. |
| 6,685,665 B2 | 2/2004 | Booth et al. |

(56) References Cited

U.S. PATENT DOCUMENTS

| | | |
|---|---|---|
| 6,692,467 B2 | 2/2004 | McFarlane |
| 6,830,578 B2 | 12/2004 | O'Heeron et al. |
| 6,835,201 B2 | 12/2004 | O'Heeron et al. |
| 6,863,674 B2 | 3/2005 | Kasahara et al. |
| 6,884,253 B1 | 4/2005 | McFarlane |
| 6,905,489 B2 | 6/2005 | Mantell et al. |
| 6,908,454 B2 | 6/2005 | McFarlane |
| 6,918,871 B2 | 7/2005 | Schulze |
| 6,939,296 B2 | 9/2005 | Ewers et al. |
| 6,942,671 B1 | 9/2005 | Smith |
| 6,960,164 B2 | 11/2005 | O'Heeron |
| 7,182,752 B2 | 2/2007 | Stubbs et al. |
| 7,250,035 B1 | 7/2007 | Ott et al. |
| 7,285,112 B2 | 10/2007 | Stubbs et al. |
| 7,297,141 B2 | 11/2007 | Kathrani et al. |
| 7,338,473 B2 | 3/2008 | Campbell et al. |
| 7,449,007 B2 | 11/2008 | Ott et al. |
| 7,455,653 B2 | 11/2008 | Ott et al. |
| 7,476,212 B2 | 1/2009 | Spearman et al. |
| 7,563,250 B2 | 7/2009 | Wenchell |
| 7,731,704 B2 | 6/2010 | Ott et al. |
| 7,744,557 B2 | 6/2010 | Ott et al. |
| 7,854,724 B2 | 12/2010 | Stearns et al. |
| 7,918,816 B2 | 4/2011 | Ott et al. |
| 8,147,442 B2 | 4/2012 | Ott et al. |
| 8,172,788 B2 * | 5/2012 | Koninckx et al. .............. 604/26 |
| 8,211,052 B1 | 7/2012 | Ott et al. |
| 8,269,638 B2 | 9/2012 | Lloyd et al. |
| 8,292,840 B2 | 10/2012 | Spearman et al. |
| 8,414,550 B2 | 4/2013 | Roberts et al. |
| 8,551,049 B2 | 10/2013 | Ott et al. |
| 2002/0013597 A1 | 1/2002 | McFarlane |
| 2002/0120226 A1 | 8/2002 | Beck |
| 2002/0128603 A1 | 9/2002 | Booth et al. |
| 2002/0143236 A1 | 10/2002 | Sauer et al. |
| 2002/0161387 A1 | 10/2002 | Blanco |
| 2002/0183715 A1 * | 12/2002 | Mantell et al. .............. 604/506 |
| 2003/0028139 A1 * | 2/2003 | Inoue .................. A61M 13/003 604/26 |
| 2003/0040711 A1 | 2/2003 | Racenet et al. |
| 2003/0045834 A1 | 3/2003 | Wing et al. |
| 2003/0158527 A1 * | 8/2003 | Mezzoli .................. A61H 35/04 604/275 |
| 2004/0034339 A1 | 2/2004 | Stoller et al. |
| 2004/0158126 A1 | 8/2004 | Sauer et al. |
| 2004/0199121 A1 | 10/2004 | Wenchell et al. |
| 2004/0204671 A1 * | 10/2004 | Stubbs et al. .................. 604/26 |
| 2004/0236340 A1 * | 11/2004 | Cirotteau .......... A61B 17/7095 606/86 R |
| 2005/0004512 A1 | 1/2005 | Campbell et al. |
| 2005/0010164 A1 | 1/2005 | Mantell |
| 2005/0015043 A1 | 1/2005 | Stubbs et al. |
| 2005/0075605 A1 | 4/2005 | Lyon |
| 2005/0107815 A1 | 5/2005 | McFarlane |
| 2005/0107816 A1 | 5/2005 | Pingleton et al. |
| 2005/0251190 A1 | 11/2005 | McFarlane |
| 2005/0261717 A1 | 11/2005 | Sauer et al. |
| 2005/0288622 A1 * | 12/2005 | Albrecht ............ A61B 17/3417 604/23 |
| 2006/0079925 A1 | 4/2006 | Kerr |
| 2006/0182637 A1 | 8/2006 | Jacobsen et al. |
| 2007/0088275 A1 | 4/2007 | Stearns et al. |
| 2008/0086160 A1 | 4/2008 | Mastri et al. |
| 2009/0137943 A1 | 5/2009 | Stearns et al. |
| 2010/0185139 A1 | 7/2010 | Stearns et al. |
| 2010/0241061 A1 | 9/2010 | Ott et al. |
| 2012/0316510 A1 | 12/2012 | Ott et al. |
| 2012/0316512 A1 | 12/2012 | Ott et al. |

FOREIGN PATENT DOCUMENTS

| | | |
|---|---|---|
| DE | 4133073 A1 | 4/1992 |
| DE | 19523685 A1 | 1/1997 |
| EP | 0484725 B1 | 5/1992 |
| EP | 0323018 B1 | 6/1993 |
| EP | 0577400 B1 | 1/1994 |
| EP | 0664992 B1 | 8/1995 |
| EP | 1188415 A3 | 5/2002 |
| EP | 1685792 A1 | 8/2006 |
| EP | 1707132 B1 | 10/2006 |
| GB | 2173312 A | 10/1986 |
| WO | WO-9411040 A1 | 5/1994 |
| WO | WO-199601132 A1 | 1/1995 |
| WO | WO-1998/19736 A1 | 5/1998 |
| WO | WO-2000/37134 A1 | 6/2000 |
| WO | WO-2002033108 A2 | 4/2002 |
| WO | WO-2001/91653 A3 | 5/2002 |
| WO | WO-2002085444 A1 | 10/2002 |
| WO | WO-2010082722 A1 | 7/2010 |
| WO | WO-2012128826 A3 | 9/2012 |

OTHER PUBLICATIONS

"Infant Flow System" from www.erne-med.co.uk.
"Air Jets and Nozzles" from www.exair.com.
Annex to Form PCT/ISA/206—Communication Relating to the Results of the Partial International Search in connection with PCT/US2006/045961 dated Jun. 15, 2007.
International Search Report issued in PCT Application No. PCT/US2007/088017, dated Mar. 9, 2009.
International Search Report and Written Opinion issued for PCT/US2007/021387 dated Jul. 30, 2008.
Office Action for European Patent Application No. 07839288.3 dated Nov. 10, 2011.
International Search Report for PCT/US2011/032305 dated May 24, 2011.
Written Opinion for PCT/US2011/032305 dated Oct. 13, 2012.
Written Opinion for PCT/US2007/088017 dated Jun. 18, 2009.
Office Action for Japanese patent Application No. 2009-527335, dated Jan. 24, 2012.
Decision of Refusal for Japanese patent Application No. 2009-527335, dated Dec. 18, 2012.
Extended European Search Report for European Patent Application No. 11152046.6, dated Apr. 12, 2011.
European Patent Office Communication for European Patent Application No. 06836756.2, dated Jul. 30, 2009.

* cited by examiner

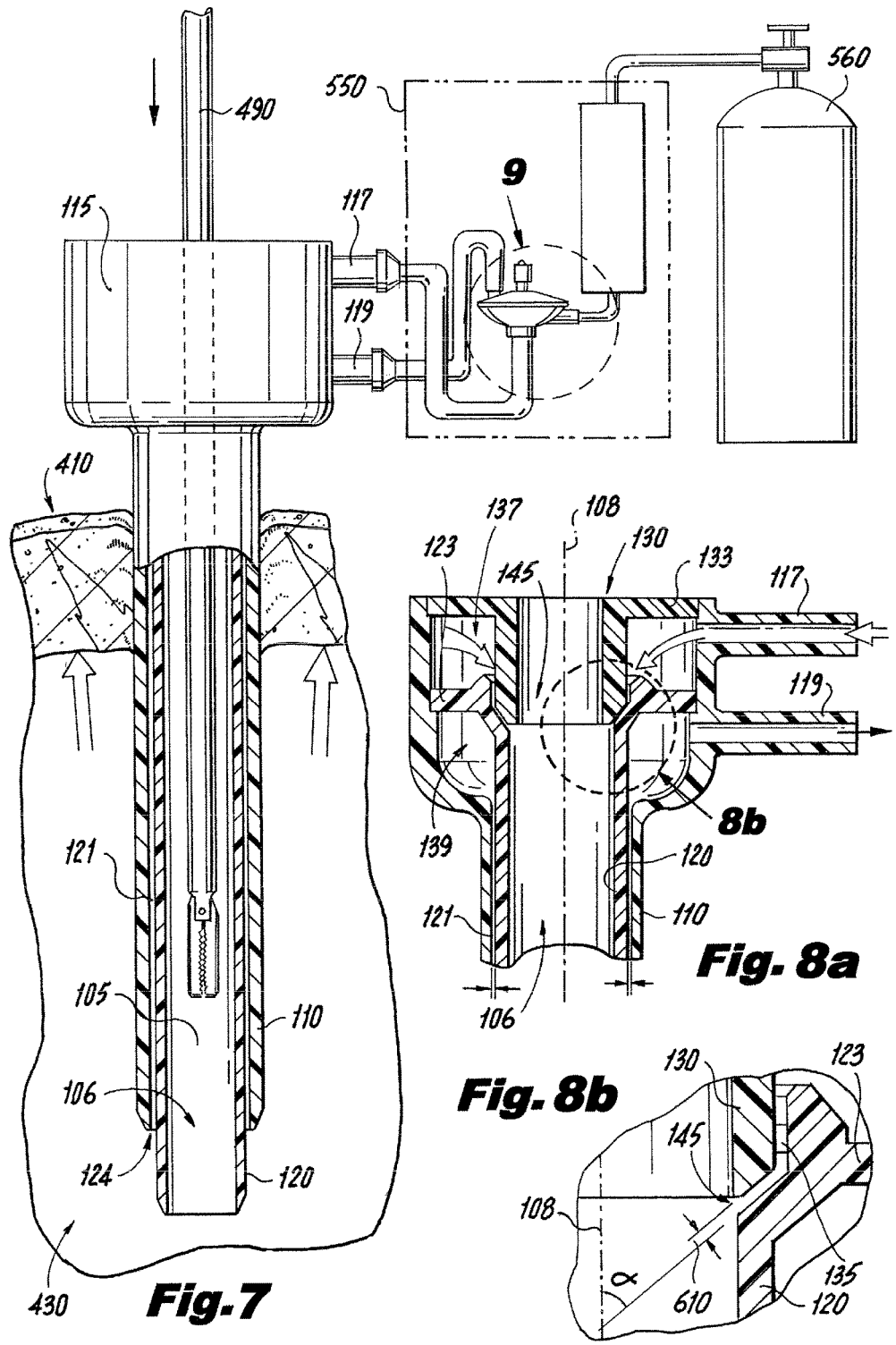

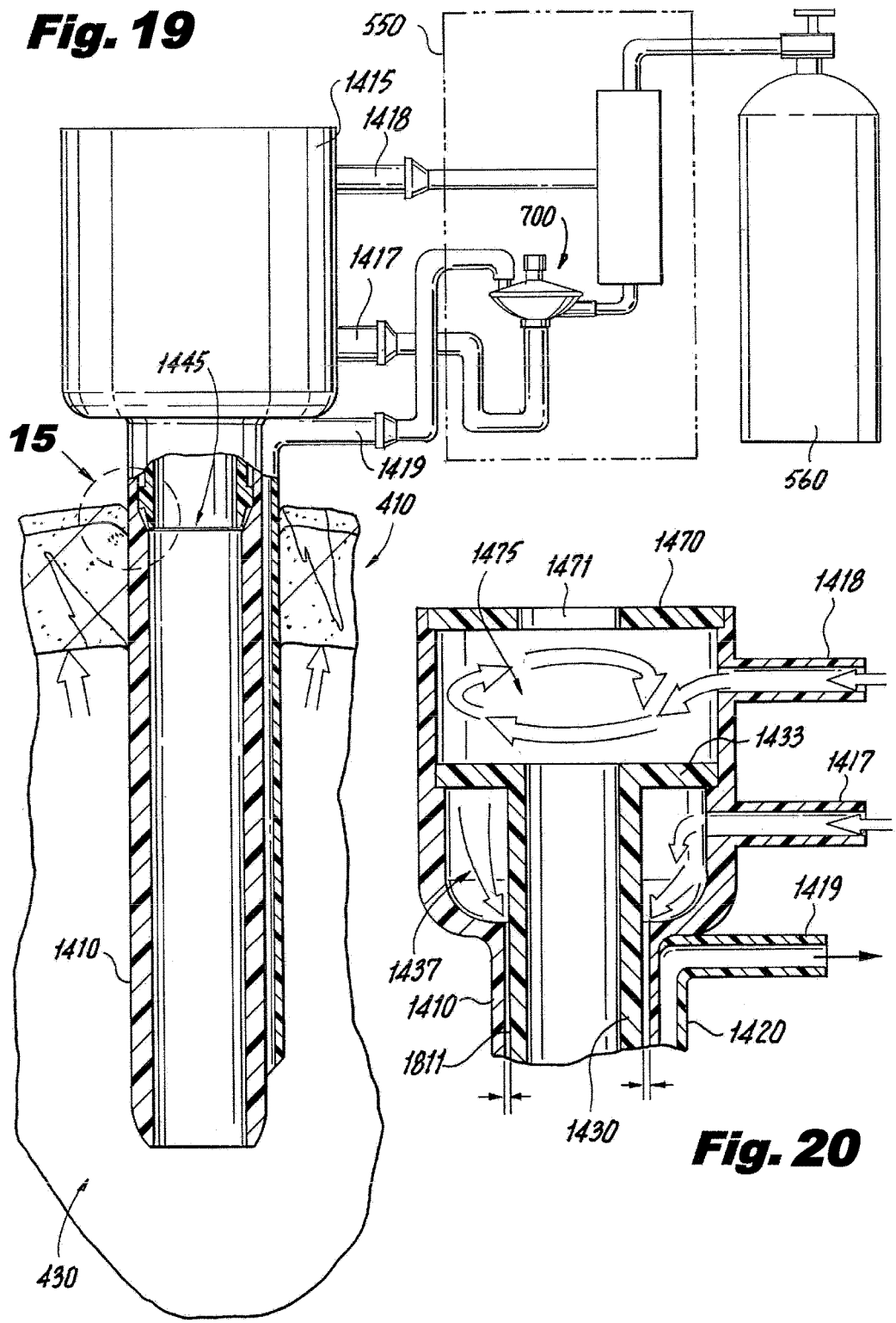

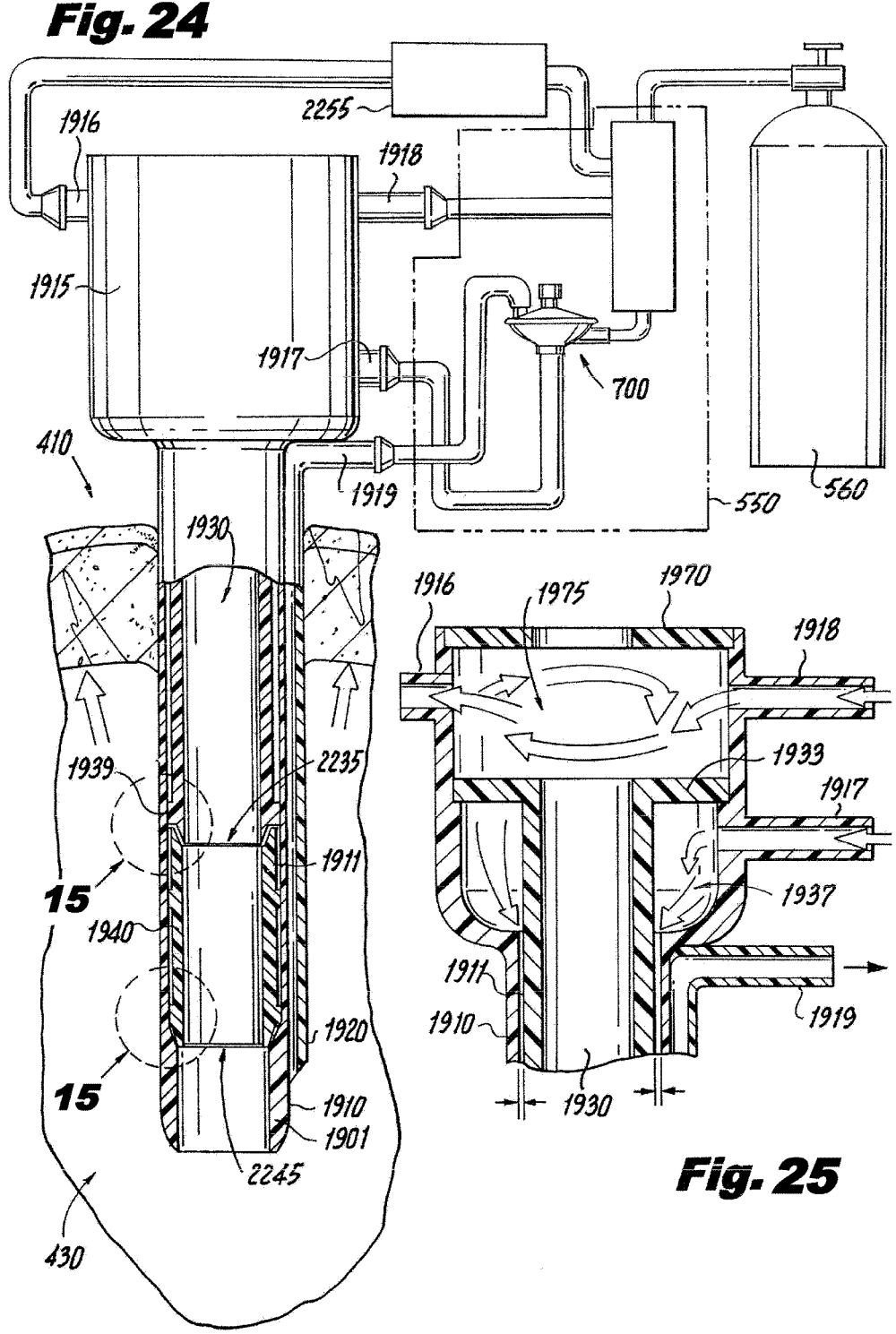

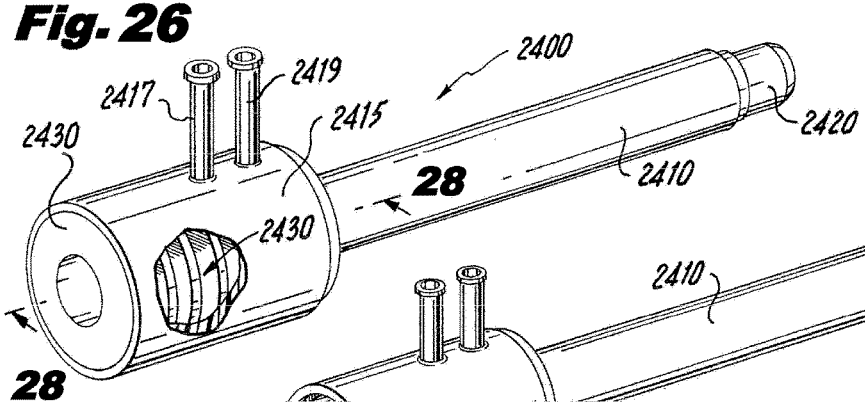
Fig. 26
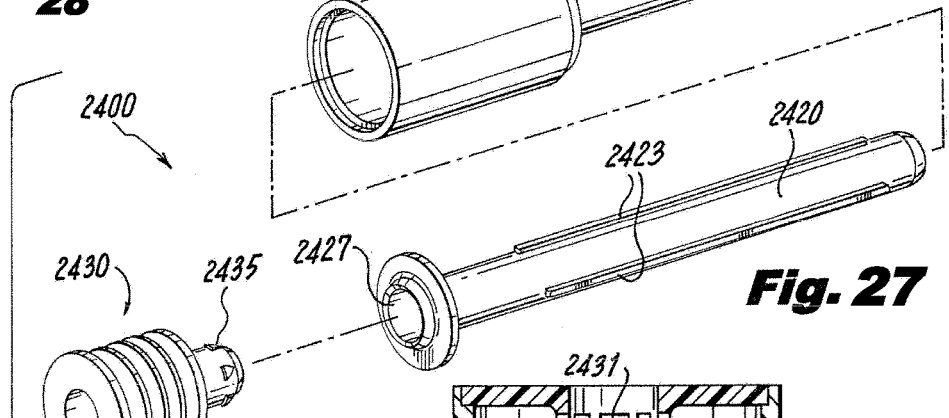
Fig. 27
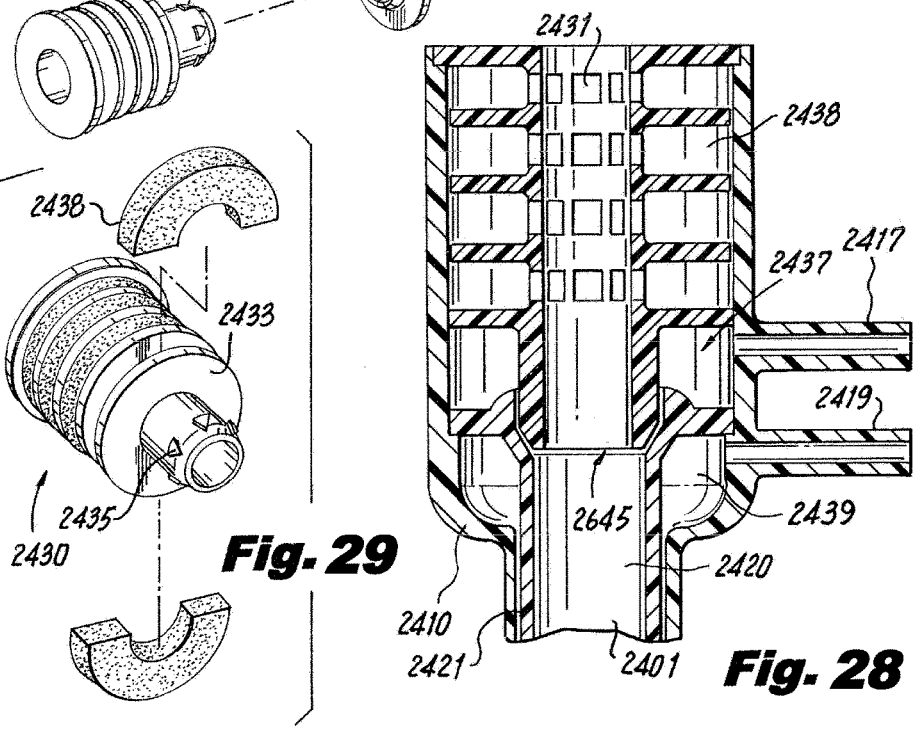
Fig. 29
Fig. 28

TROCAR ASSEMBLY WITH PNEUMATIC SEALING

CROSS-REFERENCE TO RELATED APPLICATIONS

This application is a continuation of and claims the benefit and priority to U.S. patent application Ser. No. 12/950,684, filed Nov. 19, 2010, which is a division of U.S. patent application Ser. No. 11/517,929, filed Sep. 8, 2006, which in turn is a continuation-in-part of U.S. patent application Ser. No. 10/776,923, filed Feb. 11, 2004, which is a continuation-in-part of U.S. patent application Ser. No. 10/739,872, filed Dec. 18, 2003, which is a continuation-in-part of U.S. patent application Ser. No. 10/441,149, filed May 17, 2003. Each of the foregoing applications also claims priority to U.S. Provisional Application Ser. No. 60/461,149, filed Apr. 8, 2003. Each of the foregoing applications is expressly incorporated herein by reference.

BACKGROUND OF THE INVENTION

Field of the Invention

The present invention relates to surgical devices for providing access into a body cavity of a patient during a surgical procedure, and more particularly, to a pneumatically sealed trocar assembly.

Description of the Related Art

Laparoscopic, or "minimally invasive" surgical techniques are increasingly more common in hospitals today. Benefits of such procedures include reduced trauma to the patient, reduced opportunity for infection, and decreased recovery time. Such procedures within the abdominal cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a trocar equipped to deliver insufflation fluid, or by a separate insufflation device, such as an insufflation needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the trocar devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar. However, sealing in this manner is not usually complete, such seals cannot seal between multiple instruments, and such seals also inhibit free movement of the surgical instruments and/or removal of tissue through the trocar. Such seals are also vulnerable to damage during the surgical procedure. Alternatively, a flapper valve or spring-loaded trap door can be used. However, these types of mechanical valves suffer from similar drawbacks.

Most valves, and particularly duckbill-type valves, which include resilient valve members that directly contact surgical instruments, not only interfere with the movement of surgical instruments, but reduce the ability of a surgeon to accurately sense the patient anatomy on which the surgeon is operating. Minimally invasive surgical procedures are carried out with a visualization aid such as a camera, and as a result, depth perception on the part of the surgeon is inhibited. Accordingly, the ability to physically sense resistance of structures and of tissues through movement of the surgical instruments plays an important role in a successful and safe surgical procedure. Frictional forces imparted on surgical instruments by contact of the aforementioned mechanical valves can mask the sensory signals, i.e., the haptic perception, that the surgeon might otherwise use to determine precisely what is occurring at the opposite end of the surgical instruments being used. Accordingly, improvements to sealing technologies that allow unencumbered access while maintaining a pneumoperitoneum, are desired.

SUMMARY OF THE INVENTION

The purpose and advantages of the present invention will be set forth in and apparent from the description that follows. Additional advantages of the invention will be realized and attained by the methods and systems particularly pointed out in the written description and claims hereof, as well as from the appended drawings.

In accordance with one aspect of the invention, a trocar for use in a minimally invasive surgical procedure is provided. The trocar includes an elongated body, nozzle means and means for delivering a pressurized flow of fluid to the nozzle means. The elongated body has a generally tubular configuration with coaxially arranged inner and outer walls and longitudinally opposed proximal and distal end portions, with the inner wall defining a lumen to accommodate passage of an instrument therethrough. The nozzle means is operatively associated with the inner wall of the body for directing pressurized fluid into the lumen to develop a pressure differential in an area within a region extending from a location adjacent a distal end portion of the lumen to a location adjacent a proximal end portion of the lumen, to form a fluid seal around an instrument passing therethrough.

The aforementioned fluid seal is not a mechanical seal, as set forth above in the Background section of this paper. Rather, a barrier is created to the egress of insufflation fluid from a pneumoperitoneum, which barrier consists only of fluid. As set forth above, no mechanical sealing element is necessary to create an effective seal. Any friction created due to such fluid seal is minimal in comparison with friction that would otherwise be created through the interference of mechanical valves. As a result, the haptic perception of the surgeon is essentially unencumbered, providing the surgeon with the ability to perform more accurate and safer minimally invasive procedures where insufflation of a body cavity is required.

In accordance with the invention, the inner and outer walls can be of any shape desired. For example, the walls can be cylindrical, having a circular cross-section or can have an elliptical, lenticular, oval or rectangular cross-section. Moreover, virtually any geometry is envisioned. The nozzle means can be configured to direct the pressurized fluid at an angle of between about 0 and 90 degrees with respect to a longitudinal axis of the trocar, or any angle in-between. For example, the nozzle means can direct fluid at any angle between about 0 and 90 degrees and at any one-degree increment therebetween. In one preferred embodiment, the nozzle means directs fluid at an angle between 30 degrees, 60 degrees, or at any 0.1 degree increment therebetween, for example at an angle of about 45.0 degrees. The nozzle means can be provided at a point along a longitudinal axis of the trocar body such that a fluid stream maintains a pressure gradient substantially within the lumen of the trocar. The means for delivering a pressurized flow of fluid can be a fluid passageway defined between the inner and outer walls. The nozzle means can be a substantially annular nozzle defined in the inner wall of the body. One or more nozzles can be provided, and each can be shaped substantially as a frustoconical annulus.

The nozzle means can be provided in the distal end portion and/or the proximal end portion of the trocar body. Alternatively or additionally, the nozzle means can include first and second and/or third substantially annular nozzles, longitudinally spaced from one another. Fourth and subsequent nozzles can be provided if desired. The nozzles can be spaced so that one nozzle is arranged adjacent to the other, to a distance, for example, where nozzles are arranged at opposite ends of the interior lumen of the trocar. The first and second nozzles can be spaced from one another by a distance of 1.0 mm, 15 cm, or at any 1.0 mm increment therebetween, as necessary to achieve the desired flow characteristics through the trocar.

Trocars in accordance with the invention can further include pressure sensing means for detecting a pressure within a cavity of a patient. The pressure sensing means can include a fluid passageway carried by the trocar, configured and adapted to be in fluid communication with the cavity of a patient when in use, for measuring pressure within the cavity. Such fluid passageway can be defined on an outer surface of the outer wall of the trocar body or concentrically disposed around the outer wall of the trocar body, in which case the second fluid passageway can have a substantially annular cross-section. Alternatively, the fluid passageway can be defined within the outer wall of the trocar and terminates in a substantially annular aperture defined in an outer surface of the outer wall of the trocar body.

Further, helical grooves can be provided on an inner surface of the inner wall to impart a rotation to fluid exiting the trocar. Such grooves can be provided at an angle of zero degrees, 90 degrees, or at any 0.1 degree increment therebetween, with respect to the longitudinal axis of the trocar. More preferably, such grooves can be arranged between about 15 and 75 degrees, or at any 0.1 degree increment therebetween, with respect to the longitudinal axis of the trocar.

Trocars of the present invention can further include a recirculation chamber defined in the proximal end region of the trocar body. The recirculation chamber is in fluid communication with the lumen, and configured and adapted to provide a collection region for removal and/or recirculation of fluid flowing toward the proximal end of the trocar. A collection conduit can further be provided, the conduit being in fluid communication with an outer circumferential region of the recirculation chamber to carry fluid collected thereby to a treatment means or recirculation means. Such treatment means can be configured and adapted to remove particulate and liquid matter from the fluid received from the recirculation chamber and otherwise treat the fluid. For example, treatment means can include a filter device, a settling chamber for allowing particulate matter to separate from gas, and/or a drying device such as, a cooling element for causing vapor to condense into a liquid, for removal from a gaseous flow.

Also, trocars of the present invention can include a pressure chamber defined in the proximal end portion of the trocar body. The pressure chamber can be in fluid communication with the lumen, and configured and adapted to provide a region of increased pressure to inhibit flow of fluid flowing toward the proximal end of the trocar. A gas supply port can be provided in fluid communication with the pressure chamber, for connection to a supply line to provide a gas flow sufficient to maintain a predetermined pressure within the pressure chamber. The pressure within the pressure chamber can be about 0 mmHg, 3500 mmHg, or any 0.1 mmHg increment of pressure therebetween. More preferably, the pressure can be between about 40 mmHg and about 100 mmHg. Gas supplied to the gas supply port can be the insufflation gas or can be a different fluid from the pressurized fluid used to maintain a pressure differential within the lumen and abdominal cavity. The pressure chamber can be shaped to promote formation of a fluid vortex therein. An exhaust port can further be provided for connection to an exhaust line, to carry fluid collected thereby to a treatment means and/or recirculation means.

Further, trocars of the present invention can include an inner wall made of first and second substantially tubular members, held within an outer wall, wherein a first nozzle is defined between the first and second substantially tubular members. A second substantially annular nozzle can be defined between one of the first and second substantially tubular members and the outer wall.

A cap can be provided and configured and adapted to secure to the proximal end portion of the trocar body. The cap can include a valve means, such as a duckbill-type valve, for example. The cap can alternatively or additionally include a pressure sensing means. The cap can include a conduit for fluid communication with a pressure sensing means, to detect pressure within a cavity of a patient and/or a lumen for insertion of a surgical instrument.

Further, a cap can be provided having a lumen defined within a wall of the cap, a chamber within the cap, and a ball held within the chamber. The chamber is configured and adapted to accommodate the ball, such that gas flow from the trocar body urges the ball into a position at which the ball substantially occludes the cap lumen, and such that when an instrument is inserted through the cap lumen, the ball is urged away from the cap lumen toward a periphery of the chamber.

Any trocar of the present invention can include a baffle chamber defined near the proximal end of the trocar body. Such baffle chamber can be in fluid communication with the lumen, and configured and adapted to absorb at least a portion of sound emitted from the lumen of the trocar. Such baffle chamber(s) can include a plurality of stacked baffle units, each having a central lumen positioned to be substantially coaxial with the lumen of the trocar.

A chamber can further be defined in the proximal end portion of trocar bodies of the present invention, with a ball held within the chamber. Such chambers can be configured and adapted to accommodate the ball, such that the ball can substantially occlude a proximal aperture of the lumen, and such that when an instrument is inserted into the lumen, the ball is urged away from the proximal aperture of the lumen toward a periphery of the chamber. Gas flow within the trocar body can urge the ball into a position at which the ball can substantially occlude a proximal aperture of the lumen. Optionally, one or more resilient tethers can be provided to urge the ball into a position at which the ball can substantially occlude a proximal aperture of the lumen. Alternatively, the ball can be provided with a mass sufficient so that in a substantially upright orientation, gravity urges the ball into a position at which the ball can substantially occlude a proximal aperture of the lumen.

In accordance with another aspect of the invention, a trocar is provided, including a trocar body, a first fluid passageway and a first nozzle, which can be substantially annular in shape. In accordance with this embodiment, the trocar body has a substantially elliptical inner wall and a substantially elliptical outer wall. Alternatively, the walls can be of any other desired shape. The trocar body has a proximal end and a distal end, with the inner wall defining a lumen to provide access through the trocar. The first fluid passageway is defined between the inner wall and the outer wall. The first substantially annular nozzle is defined in the inner wall, and is in fluid communication with the first fluid passageway and configured and adapted to direct a pressurized fluid into the lumen to maintain a pressure differential within the lumen, or proximate the distal end thereof. The pressure differential is capable of inhibiting proximal egress of insufflation gas from a body cavity of a patient. The inner wall and outer wall together can include two substantially tubular elements.

A trocar for providing sealable access to a pressurized patient cavity is provided having an inner tubular member, an outer tubular member and a trocar fluid seal is also provided. The inner and outer tubular members have proximal and distal ends, and the outer tubular member is substantially concentrically disposed about the inner tubular member. A trocar fluid seal nozzle is associated with the inner tubular member, and the nozzle is adapted and configured to direct a flow of fluid toward the patient cavity to prevent loss of pressure therein.

Further, a method is provided of sealing a pressurized cavity of a patient to enable a surgical procedure. The method includes providing a trocar in accordance with the invention, supplying a flow of pressurized fluid to the trocar, and inserting a surgical instrument through the lumen of the trocar, whereby the pressurized fluid supplied to the trocar forms a seal around the surgical instrument, preventing loss of pressure within the cavity of the patient. Such method can further include inserting a second surgical instrument through the lumen of the trocar, wherein the pressurized fluid supplied to the trocar seals around and between first and second surgical instruments, preventing loss of pressure from the cavity of the patient.

Additionally, a method is provided of sealing a pressurized cavity of a patient to enable a surgical procedure. The method includes providing a trocar, supplying a pressurized fluid stream to the trocar and inserting a surgical instrument through a lumen of the trocar. The trocar has means to direct a stream of fluid through a lumen of the trocar to prevent loss of pressure within the cavity of the patient, due to loss of insufflation fluid past a surgical instrument inserted therethrough. The pressurized fluid supplied to the trocar can seal around the surgical instrument, preventing loss of pressure within the cavity of the patient. The means to direct a stream of fluid can include at least a first nozzle arranged in a proximal end portion of the trocar. The means to direct a stream of fluid can include at least a first nozzle arranged in a proximal end portion of the trocar and a second nozzle arranged in the trocar, axially spaced from the first nozzle. The means to direct a stream of fluid can additionally or alternatively include at least one nozzle which extends substantially circumferentially about the lumen of the trocar.

The invention also includes a system for providing pressurized fluid, which is preferably gas to an insufflation trocar. Alternatively, the gas can include vaporized or atomized liquids mixed or suspended therein, for example. The system includes a supply for providing insufflation fluid/gas to the system, pressure sensing means for measuring a pressure inside a body cavity, a pressure reservoir for maintaining a constant output pressure to the insufflation trocar, and pressure regulating means, for regulating pressure output to the trocar. The pressurization means and pressure sensing means can be provided in a surgical insufflator. Alternatively, the pressurization means can be a compressor and the pressure sensing means can an adjustable diaphragm-type pneumatic actuator. The pressure sensing means can alternatively be an electro-pneumatic transducer.

The pressure regulating means can include a control element, for setting by a user to select a desired pressure for the surgical cavity and an electromechanical flow-control valve for adjusting a flow of insufflation gas to maintain the desired pressure within the surgical cavity. The pressure regulating means can be a two-stage pressure regulator.

The gas supply can be connected to a pressure reservoir, to supply insufflation gas thereto, a surgical insufflator can be provided to receive gas from the supply, and output pressurized gas to the reservoir, with the insufflator having a pressure sensing conduit in fluid communication with the surgical cavity. The pressure reservoir can be connected to and can supply pressurized insufflation gas through the pressure regulating means, and the pressure regulating means can allow an amount of insufflation gas into the trocar to maintain a predetermined pressure within the surgical cavity. A pressure sensing conduit can be connected between the trocar and the pressure regulating means to control the volume of insufflation gas being provided to the trocar.

Alternatively, the gas supply can be connected to the pressurization means, to supply insufflation gas thereto. The pressurization means can be provided and connected to the pressure reservoir to provide pressurized insufflation gas to the reservoir. The pressure reservoir can be connected to and can supply pressurized insufflation gas through the pressure regulating means. The pressure regulating means can allow an amount of insufflation gas into the trocar to maintain a predetermined pressure within the surgical cavity. A pressure sensing conduit can be connected between the trocar and the pressure regulating means to control the volume of insufflation gas being provided to the trocar.

A tubing kit for use in conjunction with a trocar assembly with pneumatic sealing is also provided in accordance with the present invention. The kit can include a plurality of tubes and other elements contained within a package, which is preferably sterile or capable of being sterilized. A first tube can be provided for connection between an insufflation port on the trocar and a fluid supply port on a pressure regulating means, and a second tube can be provided for connection between a pressure sense port on the trocar and a pressure sense port on the pressure regulating means. The first and second tubes can be connected along their length, or alternatively can be coaxially arranged, one inside the other. If coaxially arranged, a splitter, or another splitting separation means, such a preformed transition from coaxial to parallel tubes, would typically be necessary to enable connection to different ports on the system components.

Additionally, a third tube can be provided for connection between a proximally arranged pressure chamber on the trocar and a pressurized fluid supply. Further, an additional, fourth tube can be provided for connection to the proximally arranged pressure chamber and a recycling means for removal of fluid from the chamber. Additionally, a reservoir can be provided, for connection between the fluid supply port on the pressure regulating means and the first tube. Connection kits in accordance with the invention can be provided in a sterile package for distribution and storage, prior to use.

In accordance with another aspect of the invention, a surgical assembly is provided. The surgical assembly comprises an elongated outer tubular member having opposed proximal and distal end portions and having a longitudinal axis extending therethrough. An elongated inner tubular member having opposed proximal and distal end portions is arranged coaxially within the outer tubular member so as to form a gas flow passage therebetween. The gas flow passage extends from the proximal end portion of the outer tubular member to the distal end portion of the outer tubular member. The gas flow passage communicates with a source of humidified insufflation gas. The distal end portion of the outer tubular member is adapted and configured to discharge humidified insufflation gas from the gas flow passage into the peritoneum of a patient.

In addition, the humidified insufflation gas can be supplied to the gas flow passage through a supply conduit. The humidified insufflation gas can discharge at a constant flow into the peritoneum of a patient. The source of the humidified gas can be supplied from an external system that supplies pressurized humidified gas to the peritoneum of a patient and regulates the pressure and flow rate of the discharged gas.

In yet another aspect of the invention, a system for delivering conditioned insufflation gas is provided. The system includes a trocar assembly having an elongated outer tubular member with opposed proximal and distal end portions and having a longitudinal axis extending therethrough. The trocar assembly further includes an elongated inner tubular member having opposed proximal and distal end portions and being arranged coaxially within the outer tubular member so as to form a gas flow passage therebetween. The gas flow passage extends from the proximal end portion of the outer tubular member to the distal end portion of the outer tubular member.

The system can also include a source of conditioned insufflation gas in fluid communication with the gas flow passage of the trocar assembly. The conditioned insufflation gas can be discharged from a distal end portion of the trocar assembly into the peritoneum of a patient. The conditioned insufflation gas can be humidified and heated insufflation gas.

In accordance with still yet another aspect of the invention, a surgical assembly is provided. The surgical assembly comprises an elongated outer tubular member having opposed proximal and distal end portions and having a longitudinal axis extending therethrough. An elongated inner tubular member having opposed proximal and distal end portions is arranged coaxially within the outer tubular member so as to form a gas flow passage therebetween. The gas flow passage extends from the proximal end portion of the outer tubular member to the distal end portion of the outer tubular member. The gas flow passage communicates with a source of heated insufflation gas. The distal end portion of the outer tubular member is adapted and configured to discharge heated insufflation gas from the gas flow passage into the peritoneum of a patient.

In addition, the heated insufflation gas can be supplied to the gas flow passage through a supply conduit. The heated insufflation gas can discharge at a constant flow into the peritoneum of a patient. The source of the heated gas can be supplied from an external system that supplies pressurized heated gas to the peritoneum of a patient and regulates the pressure and flow rate of the discharged gas.

It should be noted that although the term "trocar" is used herein, the term is intended to mean a surgical access device, that allows insertion of surgical instruments, a surgeon's hand or the like, into a surgical cavity, while maintaining insufflation pressure.

It is to be understood that both the foregoing general description and the following detailed description are exemplary and are intended to provide further explanation of the invention claimed. It is also to be understood that features of each embodiment can be incorporated into other embodiments, and that optional features described in connection with one embodiment of a trocar in accordance with the invention can be incorporated into other embodiments of trocars in accordance with the invention.

The accompanying drawings, which are incorporated in and constitute part of this specification, are included to illustrate and provide a further understanding of the method and system of the invention. Together with the description, the drawings serve to explain the principles of the invention.

BRIEF DESCRIPTION OF THE DRAWINGS

So that those having ordinary skill in the art to which the subject invention pertains will more readily understand how to make and use trocar assemblies with pneumatic sealing of the subject invention, preferred embodiments thereof will be described in detail hereinbelow, with reference to the drawings, wherein:

FIG. 7 is a partial cross-sectional view of the trocar of FIG. 3, illustrating a pressure sense channel defined between tubular members and additionally illustrating a connected system, which can include an insufflation gas supply, and a pressure sensing means, for measuring the pressure within the abdominal cavity of the patient.

FIG. 8a is a detailed cross-sectional view of the proximal end of the trocar of FIG. 3, illustrating formation of a nozzle between inner tubular members, and formation of insufflation and pressure sensing plenums between the outer tubular member and respective ones of the inner tubular members.

FIG. 8b is an enlarged cross-sectional view of the nozzle region of the trocar of FIG. 3, illustrating in more detail that embodiment of a nozzle in accordance with the invention.

FIG. 19 is an operational, partial cross-sectional view of the embodiment of FIG. 16, illustrating the trocar thereof in use, inserted through the abdominal wall of a patient. A pressure sense channel is defined on an outer wall of the trocar. Also illustrated is a system, which can include an insufflation gas supply, and a pressure sensing means, for measuring the pressure within the abdominal cavity of the patient via the pressure sense channel.

FIG. 20 is a detailed cross-sectional view of the proximal end of the trocar of FIG. 16, illustrating the structure of an insufflation supply plenum between inner and outer tubular members, as well as the proximal pressure chamber, and fluid/gas supply thereto.

FIG. 24 is an operational, partial cross-sectional view of the embodiment of FIG. 21, illustrating the trocar thereof in use, inserted through the abdominal wall of a patient. A pressure sense channel is defined on an outer wall of the trocar. Also illustrated is a system, which can include an insufflation gas supply, and a pressure sensing means, for measuring the pressure within the abdominal cavity of the patient via the pressure sense channel.

FIG. 25 is a detailed cross-sectional view of the proximal end of the trocar of FIG. 21, illustrating the structure of an insufflation supply plenum between inner and outer tubular members, as well as the proximal pressure chamber, a fluid/gas supply thereto, and further illustrating a fluid/gas capture port for removal and/or recycling of exiting fluid.

FIG. 26 is an isometric view from a proximal end of a sixth embodiment of a trocar in accordance with the invention, wherein the trocar includes proximally oriented baffle chamber to reduce noise.

FIG. 27 is an exploded view of the embodiment of FIG. 26, illustrating an outer tubular member, and insert members, which cooperate to form two fluid seal nozzles and a proximal baffle chamber, respectively.

FIG. 28 is a detailed cross-sectional view of the proximal end of the trocar of FIG. 26, illustrating the structure of an insufflation supply plenum, as well as a pressure sense plenum. Further illustrated is a proximally arranged baffle chamber to reduce noise being emitted through the proximal opening of the trocar lumen.

FIG. 29 is a partial exploded view of a baffle chamber insert, which is received in the proximal end of the trocar of FIG. 26. The insert at its distal end cooperates with the more distal tubular insert to form a nozzle therebetween.

DETAILED DESCRIPTION OF PREFERRED EMBODIMENTS OF THE INVENTION

Figure 1:
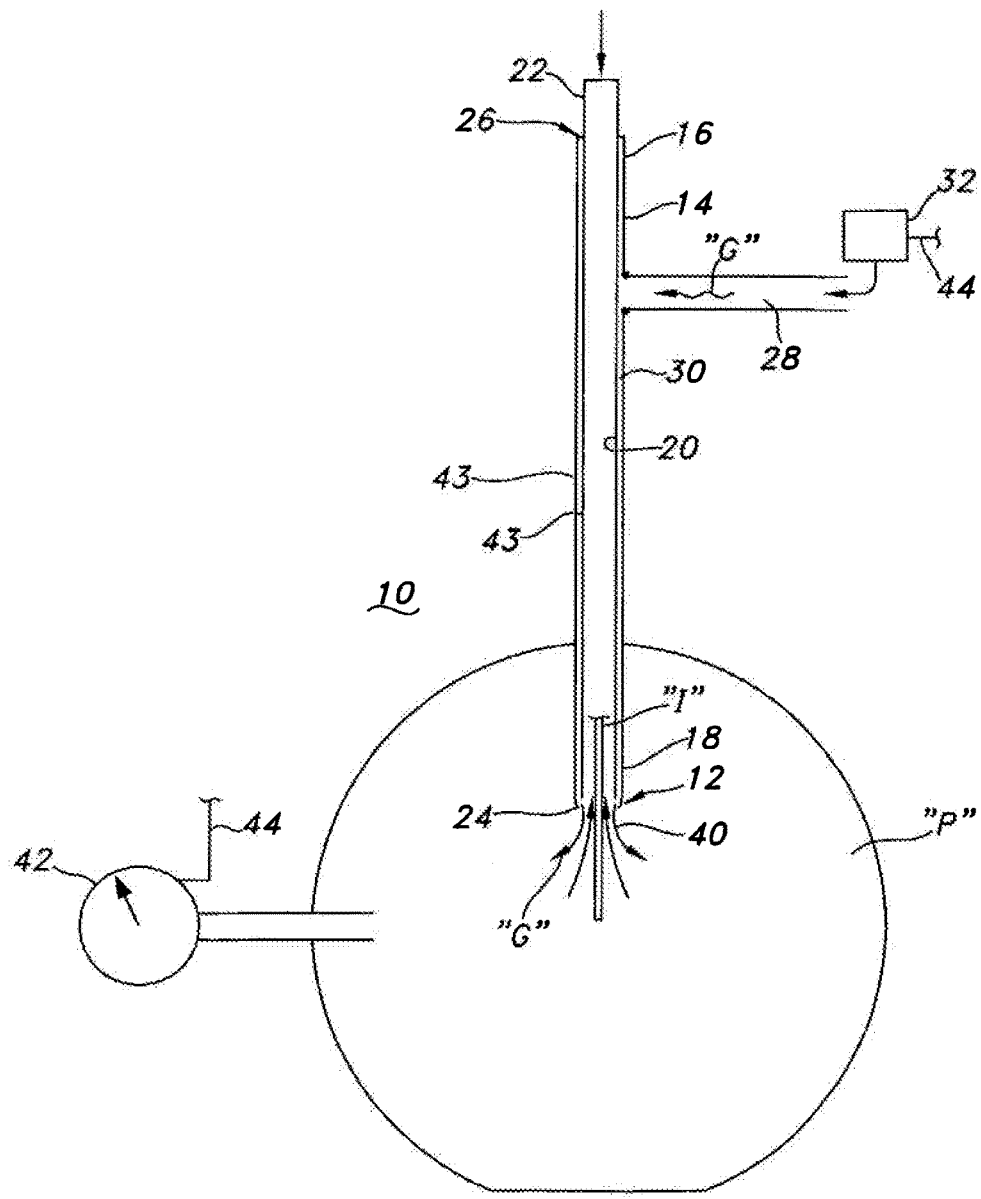
FIG. 1 is a schematic representation of an exemplary embodiment of a trocar assembly utilized within the abdominal cavity of a patient.
Figure 2:
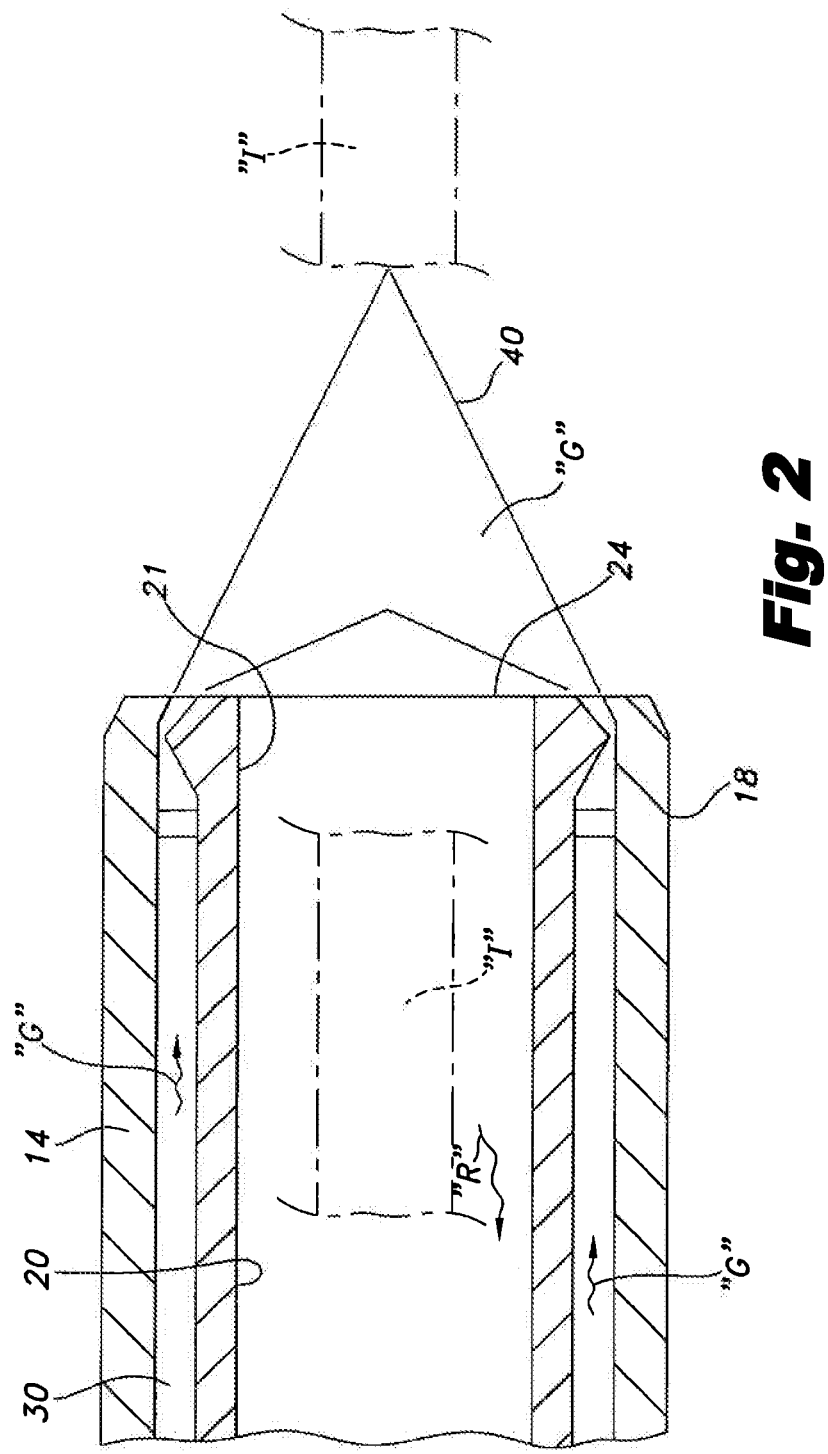
FIG. 2 is a side elevational view, in longitudinal section, of the distalmost end of the trocar assembly of FIG. 1 constructed in accordance with the present invention.
Figure 2A:
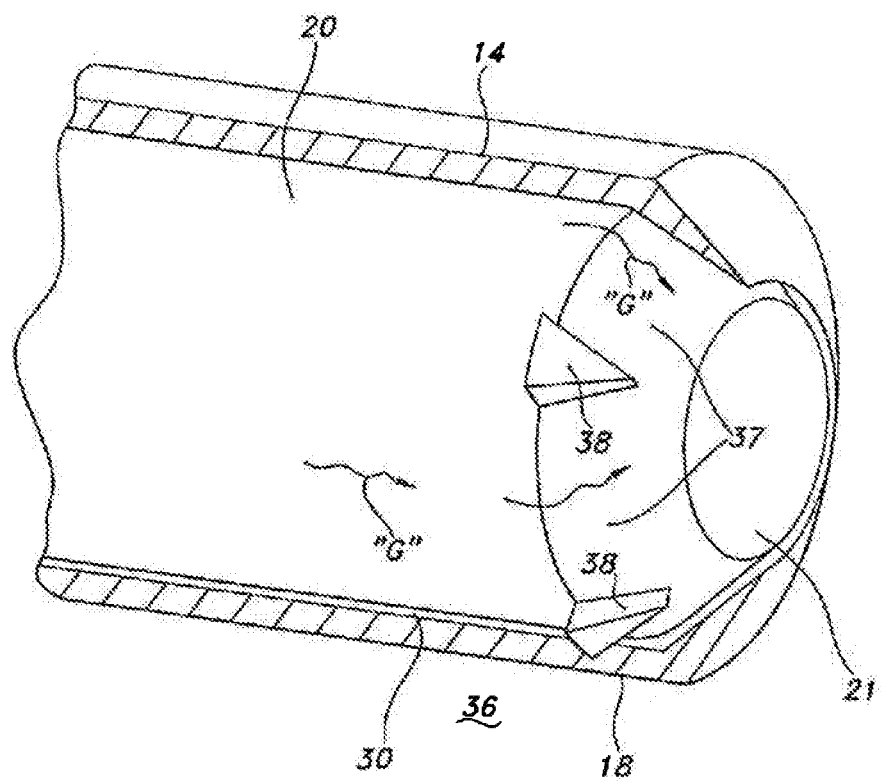
FIG. 2A is a perspective view with portions cut away, of the distalmost end of the trocar assembly of the subject invention.
Figure 3:
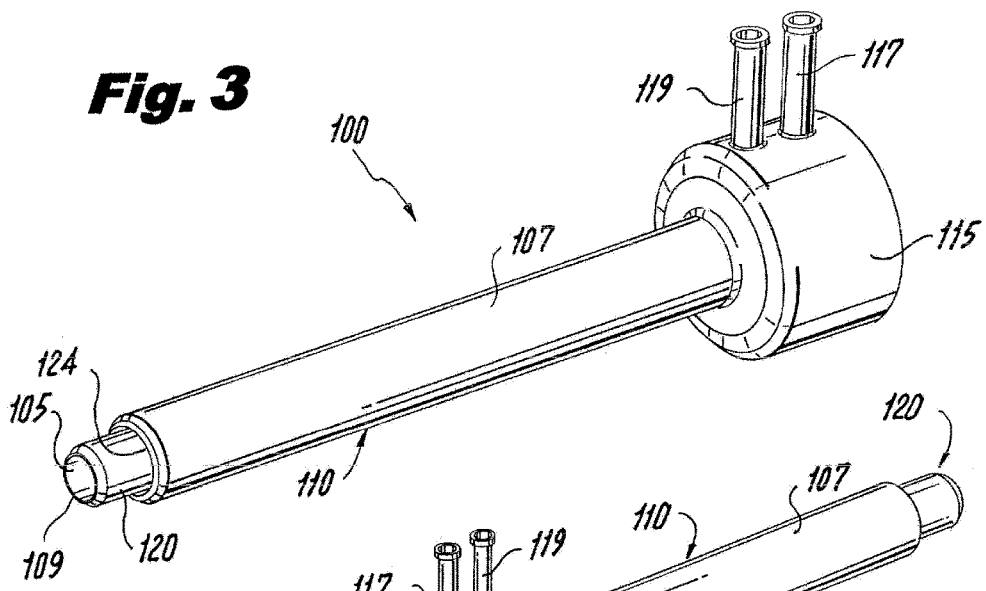
FIG. 3 is an isometric view from a distal end of an additional embodiment of a trocar including a single fluid seal nozzle, in accordance with the invention.

Referring now to the drawings, wherein like reference numerals identify similar structural aspects of the subject trocars and systems therefor, an exemplary embodiment of the pneumatically sealable trocar in accordance with the invention is shown in FIGS. 1-2A, and is designated generally by reference character 10. An additional embodiment of the trocar in accordance with the invention is shown in FIGS. 3-8 and is designated generally by reference character 100. Other exemplary embodiments of pneumatically sealable trocars in accordance with the invention, or aspects thereof, are provided in subsequent figures, which are described in detail below.

Referring now to FIG. 1, there is shown the present invention which comprises a continuous gas flow trocar assembly 10 which provides a completely open aperture 12 for the introduction of a surgical instrument "I" and its access to the peritoneum "P" without any physical contact between the innermost surface of the trocar assembly 10 and the surgical instrument "I" being introduced therewithin or withdrawn therefrom. Use of the trocar assembly 10 would also include the use of an obturator (not shown for clarity) to pierce the patient's abdomen to permit the access into the patient via the trocar assembly 10. The trocar assembly 10 of the present invention comprises an elongated outer tubular member (cannula) 14 having a first or proximal end 16 and a second or distal end 18. The assembly 10 includes an internal tubular member 20, having an open proximal end 22 and an open distalmost end 24, the internal tubular member 20 defining an innermost instrument introduction channel 21. The open proximal end 22 also comprises an access port as described herebelow. An annular seal 26 is disposed between the outer tubular member 14 and the outer walls of the inner tubular member 20 at the proximal end of the trocar assembly 10, as represented in FIG. 1.

An insufflation fluid/gas flow supply conduit 28 is in fluid communication with the annular plenum chamber 30 arranged between the outer surface of the inner tubular member 20 and the inner surface of the outer tubular member 14. Pressurized fluid/gas "G", which may be tinted, heated, chilled, humidified, de-humidified or treated with a medicament, is thus presented to the plenum chamber 30 of the continuous gas flow trocar assembly 10 via the insufflation gas conduit 28 from a regulatably controllably, pressurized source 32 for introduction into the peritoneum "P" of a patient. The insufflation fluid/gas "G" thus flows through the annular chamber 30 between the inner and outer tubular members 20 and 14 and is discharged into the peritoneum "P" of the patient through, in one preferred embodiment, a generally adjustable annular nozzle 36 arranged at the second or distal end 18 and of the trocar assembly 10.

The distal end 18 of the trocar assembly 10 defines the annular fluid flow nozzle arrangement 36, as is more clearly represented in FIG. 2. In one preferred embodiment of the nozzle arrangement 36, an array of radially outwardly extending fluid directing spacers, vanes or jets 38 are arranged to direct the insufflation/treatment fluid/gas "G" flowing therethrough, in a cylindrical stream in the annular plenum chamber 30 and through the annular nozzle arrangement 36 to discharge therefrom, as for example, in a cylindrically (preferably cone) shaped gas stream or wall of fluid or gas 40 exiting the annular arrangement of arcuate openings 37 between those jets or vanes 38, as shown in FIG. 2A.

In this continuous gas flow trocar assembly 10, the force produced by the jet fluid is counterbalanced by the pressure inside the peritoneum "P" of the patient as sensed by a pressure sensor 42, extending into the peritoneum "P", as represented in FIG. 1. The pressure sensor 42 is in proper communication with the computer controlled pressure source 32 by a communication line 44. This balance is achieved when the abdominal pressure by the inflow of insufflation fluid/gas "G" is reduced until the desired peritoneal pressure just balances the inlet air flow force as generated by the pressure source 32. The inlet fluid/gas "G" flow will maintain the correct insufflation pressure within the patient's abdomen and may be automatically controlled by computer means with the pressure source 32 so as to adjust to fluid/gas flow to allow laparoscopic medical instruments to be passed through the inner tubular member 20 into the peritoneum and to be retrieved from the abdomen through that inner tubular member 20 of the trocar assembly 10. In a further embodiment, a pressure sensor 43 may be arranged within the inner tubular member 20 or within the outer tubular member 14, or both, as represented in FIG. 1.

Outflow of returned pressurized fluid/gas "R" is effected between the medical instrument "I" within the inner tubular member 20 and the inner walls of the inner tubular member 20 and exiting out the access port 22 at the proximal end 16 of the trocar assembly 10, as represented by the letter "R" in FIG. 2.

The (those) medical instrument(s) "I" accessing the peritoneum through the inner tubular member 20 of the trocar assembly 10 and into the patient merely passes through the gaseous fluid wall 40 created by the pressurized fluid forced through the annular nozzle arrangement 36 at the distalmost end 18 of the trocar assembly 10. Manipulation of that (those) medical instrument(s) "I" is (are) not interfered with nor is removal of any tissue through that inner tubular member 20 hindered in any way by any trap door or overlapping seal arrangement typical of the prior art. The cannula or inner tubular member 20 may be movable relative to the outer tubular member 14 of the trocar assembly 10, as will be described more fully hereinbelow, to permit a slight changing of the flow of gases "G" through the annular nozzle 36 arranged within the distal end 18 of the trocar assembly 10.

FIGS. 7 and 8a illustrate an additional embodiment of trocar assembly 10. Trocar 100 includes an elongated body having an outer tubular member 110, and a coaxial inner tubular member 120. The inner tubular member 120 includes an inner surface 105 surrounding a lumen or channel 106, through which an instrument (e.g., instrument 490) can be inserted into a cavity, such as abdominal cavity 430 of a patient. Spiral or helical grooves can be provided in the surface 105 of the trocar to impart a rotation to fluid either entering or exiting the trocar. Such spin can help separate liquid or other particulate matter from fluid exiting the trocar from its proximal end, thereby facilitating collection of such waste. The outer tubular member 110 includes an outer surface 107, which in use, contacts the abdominal wall 410 of a patient through which the trocar 100 is inserted. An opening 109, which is at the distal end of the lumen 106, allows passage of a surgical instrument or a plurality of instruments into, and communication of insufflation gas with the abdominal cavity 430. The proximal end portion of the trocar 100 includes an expanded diameter portion 115, which provides space for certain functional elements of the trocar. As best seen in FIG. 8a, these functional elements include an insufflation plenum 137 and pressure sense plenum 139. Other embodiments, described in detail below, include additional functional elements.

Referring in-particular to FIG. 8a, the trocar 100 includes at its proximal end portion, a nozzle 145, in fluid communication with the lumen 106 and the insufflation plenum 137. The plenum 127 is supplied with insufflation gas through an insufflation port 117, to which insufflation gas is supplied from an external system, described in further detail below. Insufflation gas entering through the insufflation port 117, through a conduit 440 (e.g., see FIG. 6) enters the insufflation plenum 137, where it is distributed to the nozzle 145. As illustrated, the nozzle 145 is substantially annular and is defined between the inner tubular member 120 and an inner tubular insert 130.

The precise configuration of nozzles for use with trocars in accordance with the invention can vary. If desired, a plurality of discrete nozzle apertures can be defined in place of the annular nozzle 145. These discrete nozzle apertures can be arranged as necessary, about the wall of the trocar, to form an effective barrier to proximal egress of insufflation gas from the abdominal cavity of the patient. Such discrete nozzles can each be substantially round in shape, or alternatively can be oblong or another shape. The nozzles can be places at regular intervals about the circumference of the lumen, can extend part way around, or can be spaced from each other in groups. If turbulence is desired, surface features such as protrusions, vanes, grooves, surface texture can be added in the path of fluid flow, as desired.

Figure 5:
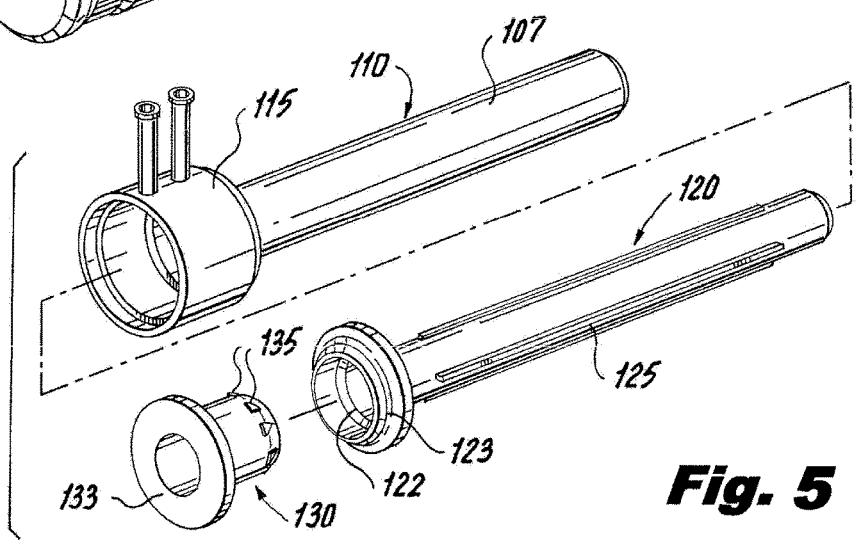
FIG. 5 is an exploded view of the embodiment of FIG. 3, illustrating inner and outer tubular members, which cooperate to form fluid channels and a fluid seal nozzle therebetween.
Figure 6:
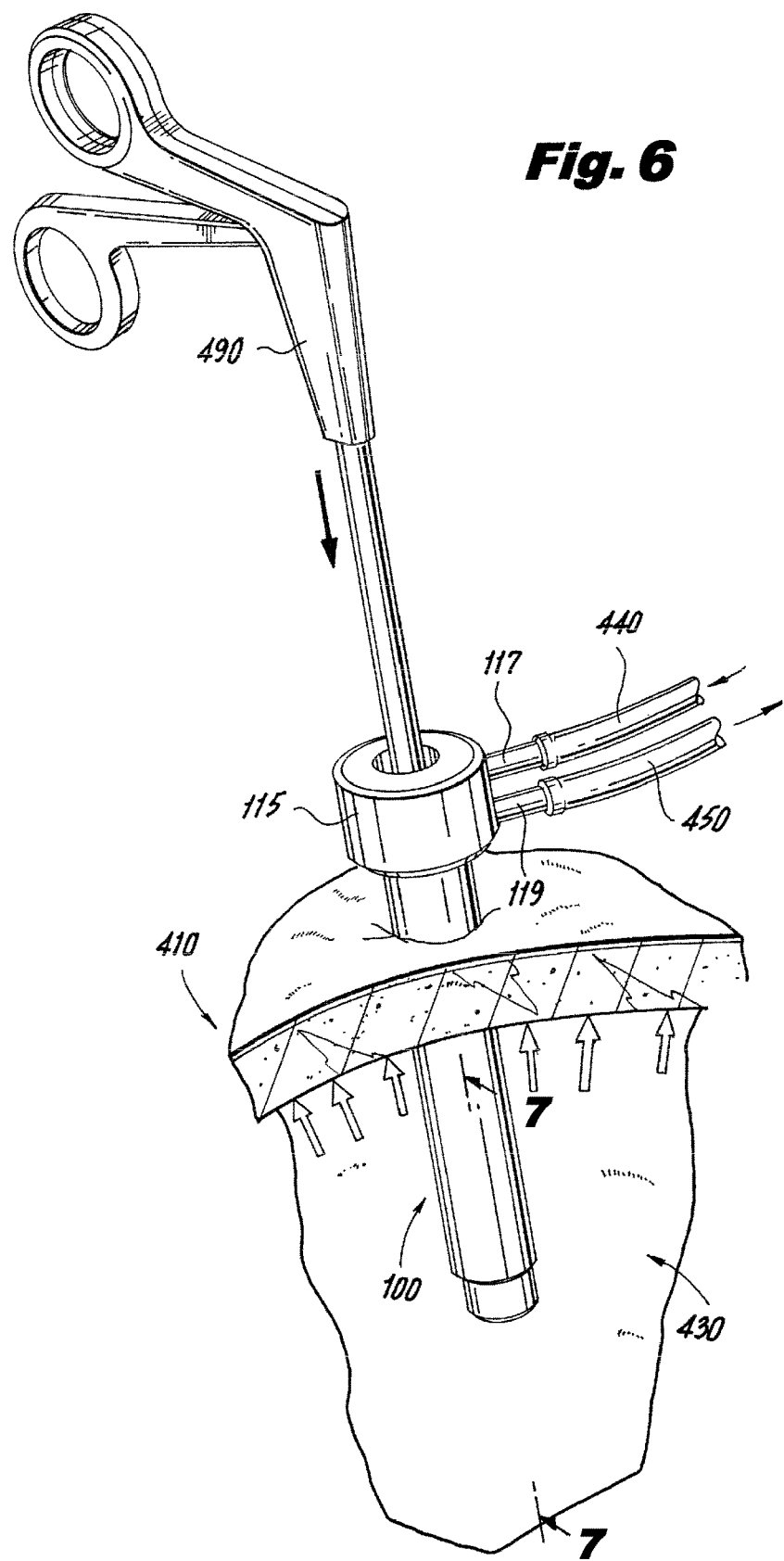
FIG. 6 is an operational view of the embodiment of FIG. 3, illustrating the trocar of FIG. 3 in use, inserted through the abdominal wall of a patient, with a surgical instrument inserted therethrough.

As best seen in FIG. 5, standoffs 135 can be provided to maintain a desired nozzle width. The standoffs 135 can be formed such that they have little or no effect on the flow of insufflation gas entering the central channel 106. Alternatively, the standoffs 135 can be configured such that they affect fluid flow in a desired manner, such as by enhancing laminar flow or turbulent flow of insufflation gas. The distal portion of the tubular insert 130 or standoffs 135, if they are provided, abut a seat portion 122 of the inner tubular member 120, thereby forming the nozzle 145, which here, appears essentially as a gap along the interior wall 105 of the trocar 100. In this and other embodiments, standoffs can alternatively or additionally be provided in an abutting portion of the inner tubular member 120, or other corresponding component. Standoffs can be arranged at any location desired, including in the nozzle itself.

The thickness 610 (See FIG. 8a) of the nozzle 145 is preferably between about 0 and $^{10}/_{1000}$ inch, more preferably about $^{2}/_{1000}$ inch, for a trocar having a lumen diameter of about 12.7 mm and a length of between about 100 mm and 120 mm. However, lumen diameters of trocars in accordance with the invention can range from about 3.0 mm and about 100 mm, at any 1.0 mm increment therebetween, inclusive, to accommodate insertion of, for example, a surgeon's hand. Lengths for trocars in accordance with the invention can range from about 50 mm to about 400 mm, at any 1.0 mm increment therebetween, inclusive, for trans-esophageal or trans-anal applications. However, the precise size of lumen diameter, and length, and nozzle thickness can vary as desired or necessary. For example, for lumens with larger cross-sectional diameters, a larger nozzle, capable of outputting a larger volume of insufflation fluid/gas may be desirable. While one nozzle is illustrated in this embodiment, other embodiments include two or more nozzles. The precise number of nozzles can be as many as desired. This can be done to create a series of pressure differentials at different axial locations along the length of the trocar 100, in order to better inhibit escape of pressure from the abdominal cavity 430.

Moreover, if desired, the nozzle width can be adjustable, allowing a user to adjust the precise volume of air entering through the nozzle. Adjustability can be accomplished by providing, for example, threads on the outer edge of the tubular insert 130, with corresponding threads on the inner edge of expanded-diameter portion 115 of the trocar 100 (See FIG. 8a).

A pressure sense channel 121 is also formed between the inner tubular member 120 and the outer tubular member 110. Standoffs 125 can be provided to maintain the desired width of opening of the pressure sense channel 121. The pressure sense channel 121 terminates in a substantially annular opening 124 in a distal end portion of the trocar 100, and at a pressure sense plenum 139 formed in the proximal end portion of the trocar 100. As illustrated, the pressure sense plenum 139 is defined between the inner tubular member 120 and the expanded diameter portion 115 of the outer tubular member 110, although other configurations are possible, as described below. Structurally, the insufflation plenum 137 and the pressure sense plenum 139 are separated by an expanded diameter portion 123 of the inner tubular member 120. An expanded-diameter portion 133 of the insert 130 similarly serves as an upper wall for the insufflation plenum, however variations of this configuration are possible. The distal pressure sense aperture 124, which is the distal termination of the pressure sense channel 121, communicates with the gas in the abdominal cavity 430 of the patient. The pressure in the channel 121, is thus the same as in the patient's abdominal cavity 430. Accordingly, the pressure in the pressure sense plenum 139 is also equal to the pressure within the abdominal cavity 430. The pressure sense port 119, which is in fluid communication with the pressure sense plenum 139, is in-turn, connected to a pressure sensing device, which is part of the system 550, via pressure sense conduit 450. The pressure sensing device can be a surgical insufflator, electronic pressure transducer or a diaphragm valve (e.g., see FIG. 9a), for example.

Insufflation gas is provided from a supply, such as a tank 560. A system 550, which can include elements such as an insufflator, reservoir, pressure regulator, conditioning elements, such a humidifier, dehumidifier or heater, recirculation devices and/or flow booster, receive the insufflation gas. The system pressurizes the gas to the desired pressure and treats or conditions the gas as necessary. As set forth above, the pressure supplied to trocars in accordance with the invention can be between about 0 mmHg and 3500 mmHg at any 0.1 mmHg increment of pressure therebetween. Such pressures are suitable for pressure chambers such as chamber 1475 of FIG. 20. However, relatively high pressures can also be supplied to the nozzles of trocars in accordance with the invention, such as nozzle 145 in FIG. 8a. In one embodiment, pressure supplied to the nozzle(s) is between about 1000 mmHg and about 2000 mmHg, and can be at any 0.1 mmHg increment of pressure therebetween. In one preferred embodiment, the pressure supplied to the nozzle(s) is about 1530 mmHg. Naturally, pressures can vary as needed or desired.

The trocar 100 is connected to the system 560 by way of at least one conduit, which supplies the insufflation gas to the insufflation plenum 137. The pressurized gas then passes into and through the nozzle 145, into the central channel 106. The precise configuration of the nozzle 145 can vary, but in any case inhibits flow of insufflation gas from the abdominal cavity 430 of the patient. The angle of the nozzle, with respect to a longitudinal axis 108 of the trocar 100 is designated herein as α (alpha). Such angle α can vary from 90 degrees, where a gas jet is injected across the channel 106, to 0 degrees where a gas jet is formed parallel to the interior wall 105 of the trocar 100, or can be an angle any increment of 0.1 degree therebetween. Typically, the angle α will be greater than 0 and less than 90 degrees. In some embodiments, the angle α is preferably between about 0 and 10 degrees, but the precise value can depend on the length of the trocar. In a preferred embodiment, the angle of the nozzle will approach 0 degrees, in cases where a relatively long trocar, or cannula is provided (such as trocar for trans-esophageal use). In instances where the trocar is relatively short, an angle approaching 90 degrees can be selected.

In accordance with a preferred embodiment of the invention, the nozzle 145 forms a jet of pressurized fluid, such as a pressurized gas, that is directed toward the distal end of the trocar 100. Such jet can be substantially conical if desired. While the abdominal cavity 430 is being filled with insufflation gas, the gas from the nozzle 145 passes down the channel 106 of the trocar 100, and into the abdominal cavity 430. The pressure within the abdominal cavity 430 will eventually reach equilibrium with the pressure of the gas provided by the trocar 100, at which time the abdominal cavity 430 of the patient will essentially cease expansion, as no additional volume of gas will be able to enter the cavity. The gas ejected from the nozzle 145 will be directed distally, and any additional fluid entering the abdominal cavity 430 will displace fluid already in the cavity 430. Excess insufflation gas, or displaced gas will exit from the proximal end of the trocar 100. In effect, what is created is a region in which the force of gas entering from the nozzle 145 at least equals that of the force of pressure within the abdominal cavity, acting in the region of the lumen 106. A pressure gradient is created and maintained by the trocar 100, between the pressure of the abdominal cavity 430 and that of the surrounding environment, such as that of an operating room. As mentioned above, if a plurality of nozzles (e.g., nozzle 145) are provided, then a plurality of pressure zones can be created, limiting the burden on any one nozzle to create and maintain a large pressure differential.

With insufflation fluid/gas being provided and distributed about the circumference of the inner wall 105 of the trocar 100, a single surgical instrument 490 or a plurality of instruments, can be inserted through the lumen 106 of the trocar 100. The pressurized fluid entering from the nozzle 145 will simply flow around the one or more instruments 490 and/or between adjacent instruments inserted through the channel 106, and maintain pressure within the abdominal cavity 430. Since the nozzle(s) encircle each instrument, pressurized insufflation gas can impinge and be directed completely around each surgical instrument. Accordingly, a reliable fluid seal is achieved.

Further, the fluid seal is capable of sealing around cables, around and within bundles of cables, or any other object inserted through the lumen of the trocar. If no instrument or object is inserted through the lumen, the seal is still maintained. Accordingly, a surgeon can have an unobstructed view through the trocar and into the abdominal cavity of the patient, while still maintaining a seal for pressure of the abdominal cavity. Heretofore such unobstructed view has been impossible.

An additional benefit of the devices set forth herein, is that during a procedure, the insufflation fluid can be set to flow at a velocity such that the fluid can clean remove debris from an instrument in the fluid flow, particularly at regions of higher velocity. The speed of the fluid flow will typically be highest at the location of a nozzle. For example, if a fiber-optic camera is inserted through the lumen of the trocar and into the abdominal cavity of a patient, and such lens becomes soiled, the surgeon need only move the lens temporarily into the path of the fluid seal fluid flow, to blow any debris off of the lens. Accordingly, the lens need not be removed for cleaning.

While the present trocar 100 is capable of providing insufflation gas into an abdominal cavity 430 of a patient, it is to be understood that alternatively, a secondary insufflation device can be used to provide the initial insufflation of the abdominal cavity, with the trocar 100 being used mainly to provide sealable access to the abdominal cavity 430.

Figure 4:
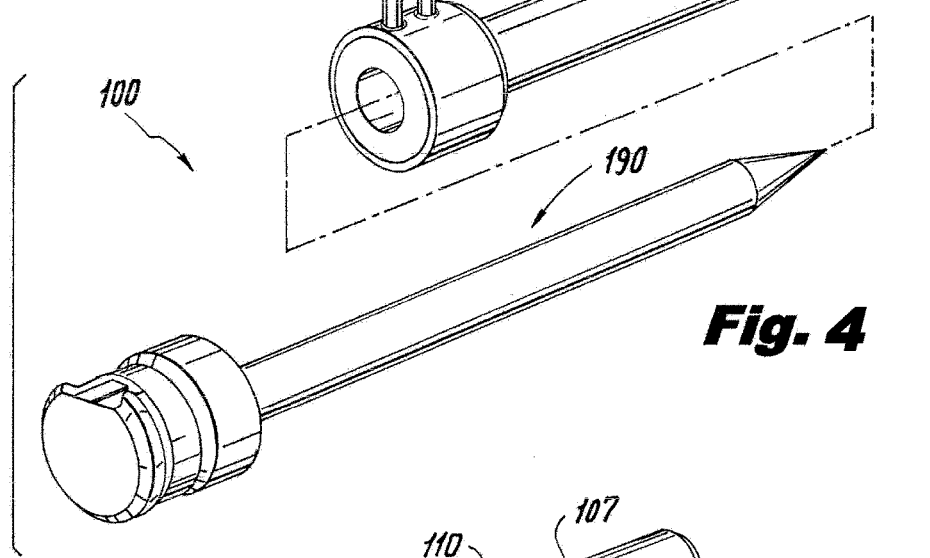
FIG. 4 is an isometric view from a proximal end of the embodiment of FIG. 3, illustrating the trocar and a removable inserter which, when inserted through the central lumen of the trocar, facilitates insertion of the trocar through the abdominal wall of a patient.

As best seen in FIG. 4, an obturator 190 or inserter can also be provided, and can be used to facilitate insertion of the trocar 100 into the abdominal cavity 430 of the patient. The obturator 190 can be of any type desired, including but not limited to blunt tip obturators.

As discussed briefly above and in more detail below, subject trocars are supplied with insufflation fluid/gas from an external system. Such systems, e.g., system 550, can include elements such as an insufflator, reservoir, pressure regulator, conditioning elements, such a humidifier, dehumidifier or heater, recirculation devices and/or flow booster, receive the insufflation gas. The trocar 100 is connected to the system 560 by way of at least one conduit, which supplies the insufflation gas to the insufflation plenum 137. The trocar can be connected directly to a pressure-sensing flow booster valve, such as that illustrated in FIGS. 9a-9c.

Figure 9A:
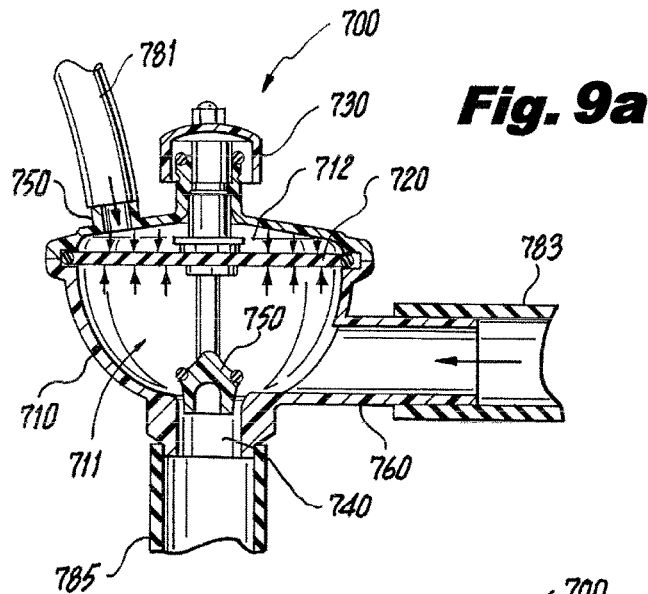
FIG. 9a is a cross-sectional view of a flow control valve in accordance with the invention, illustrating a state where pressures in chambers on each side of a dividing membrane are experiencing equal pressures, leaving a valve plunger in a first position.
Figure 9B:
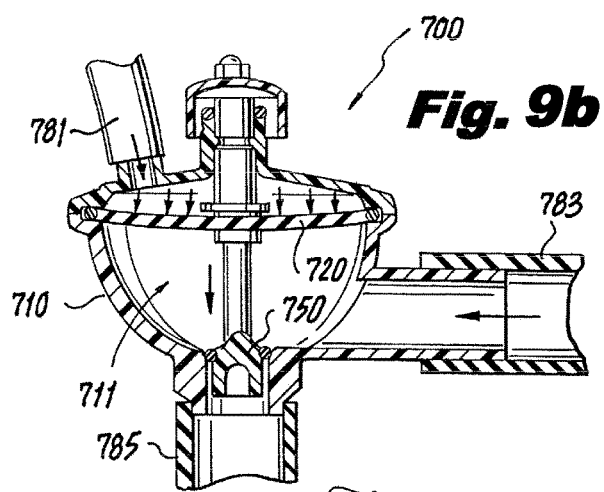
FIG. 9b is a cross-sectional view of the flow control valve of FIG. 9a, illustrating a state where pressure in the upper chamber is higher than pressure in the lower chamber, causing the valve plunger to obscure a lower aperture, thereby stopping fluid flow through the lower chamber of the valve.
Figure 9C:
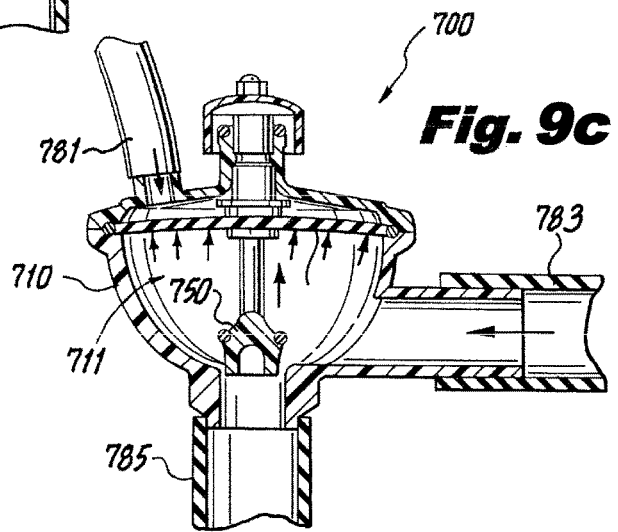
FIG. 9c is a cross-sectional view of the flow control valve of FIG. 9a, illustrating a state where pressure in the upper chamber is lower than pressure in the lower chamber, causing the valve plunger to move upwardly, thereby increasing fluid flow through the lower chamber of the valve.

FIGS. 9a-9c illustrate three states of a diaphragm valve 700 that can be used in conjunction with trocars in accordance with the present invention. The valve 700 includes a housing 710, and a diaphragm 720, which separates the housing 710 into two chambers 711, 712. The upper chamber 712 is a pressure sense chamber, which includes a pressure sense port 750 in fluid communication with the abdominal cavity 430 of the patient, by way of, for example, a pressure sense channel 121 and pressure sense conduit 781 of a trocar in accordance with the invention. A supply conduit 783 is attached to inlet port 760, which receives a supply of pressurized insufflation gas from, for example, a compressor. The outlet port 740 is connected via a conduit 785 to an insufflation port (e.g., port 117) of a trocar in accordance with the invention.

The valve 700 adjusts flow through the lower chamber 711, depending on the pressure sensed by the upper chamber 712. A knob and spring arrangement 730 can be adjusted to bias the diaphragm to a position, such that a desired set point is achieved. As can be seen, if the pressures of both chambers are equalized, then the plunger 750 of the valve 700 remains in a predetermined position, which in this embodiment is a slightly open position, as illustrated (See FIG. 9a). Alternatively, this criteria can result in a closed valve 700 if it is adjusted accordingly. As illustrated, if the pressure sense line and chamber 712 experience a pressure increased over that of the supply pressure of lower chamber 711, the valve can be set to close under these circumstances (See FIG. 9b). Similarly, as seen in FIG. 9c, if the pressure in upper chamber 712 drops, with respect to the supply pressure, the diaphragm 720 moves upward, moving plunger 750 upward and opening the valve 700, causing increased fluid flow out of outlet port 740, and into the a insufflation trocar.

Figures 13, 14, 15:
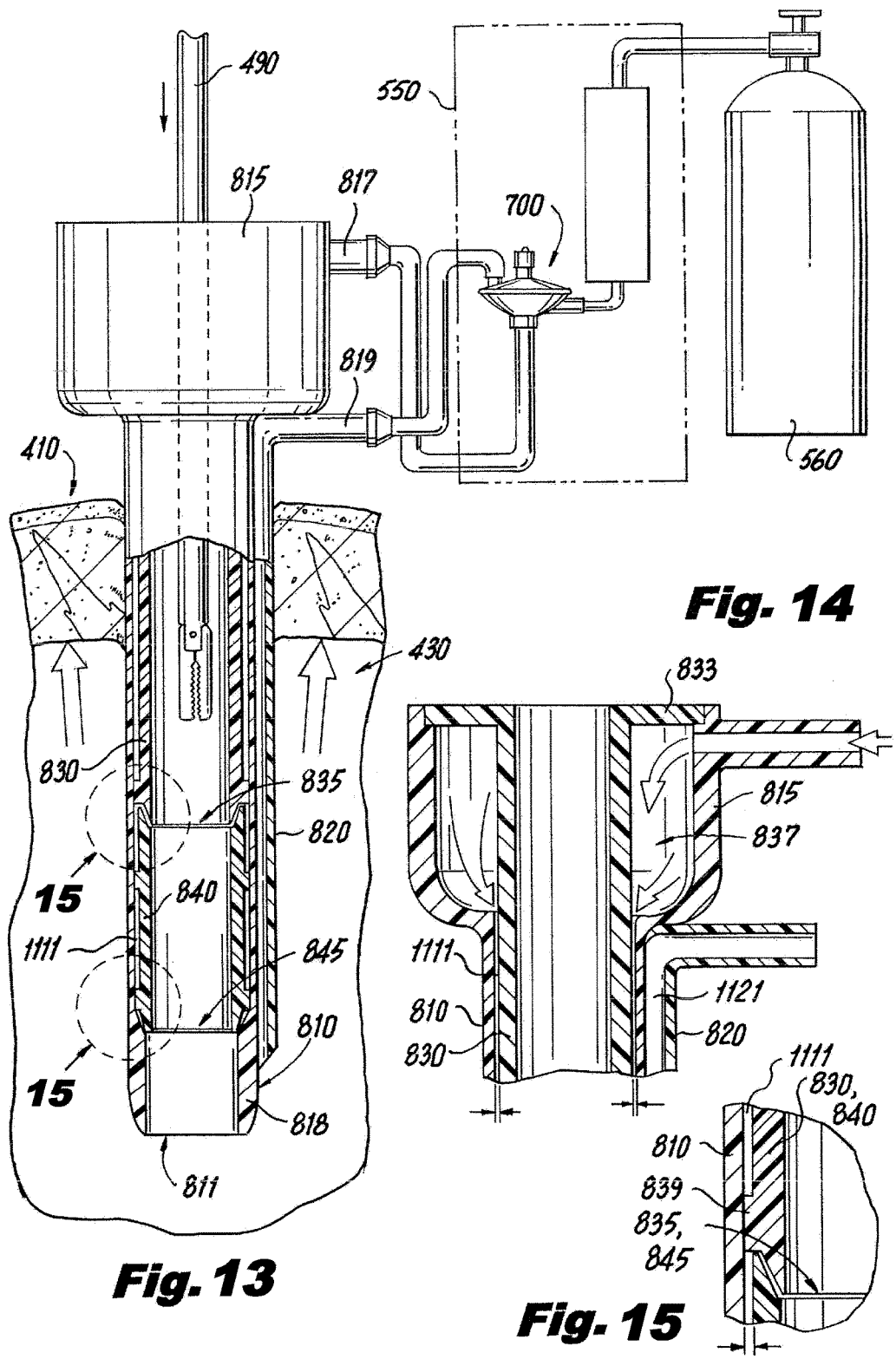
FIG. 13 is an operational, partial cross-sectional view of the embodiment of FIG. 10, illustrating the trocar thereof in use, inserted through the abdominal wall of a patient, with a surgical instrument inserted therethrough. A pressure sense channel is defined on an outer wall of the trocar. Also illustrated is a system, which can include an insufflation gas supply, and a pressure sensing means, for measuring the pressure within the abdominal cavity of the patient via the pressure sense channel.
FIG. 14 is a detailed cross-sectional view of the proximal end of the trocar of FIG. 10, illustrating the structure of an insufflation supply plenum between inner and outer tubular members.
FIG. 15 is a detailed view of the respective region of FIG. 13, illustrating in further detail the structure of nozzles in accordance with this embodiment of the invention.

Referring to FIGS. 10-15 another trocar constructed in accordance with the invention is illustrated and is designated generally by reference numeral 800. The trocar 800 differs from the trocar 100 of FIGS. 3-8 in placement and quantity of nozzles 835, 845, as well as in the configuration of the pressure sense channel 820. As best seen in FIGS. 13 and 14, a tubular body member 810 is provided, which includes an expanded diameter proximal end portion 815 that houses the insufflation plenum 837, and a distal opening 811 at its distal end, which allows access to and fluid communication with the abdominal cavity 430 of the patient. An expanded diameter end portion 833 of the proximal insert member 830 helps seal and define the insufflation chamber 837 from the surrounding environment. As embodied, two tubular insert members 830, 840 are provided. A lower, more distal nozzle 845 is defined between an increased thickness portion 818 of the body member 810, and the most distal tubular insert 840. A second, more proximal nozzle 835, is defined between the proximal edge of the distal tubular insert 840, and the distal edge of the proximal tubular insert 830.

As with the foregoing embodiment of trocar 100 of FIGS. 3-8, and other embodiments described herein, standoffs 839 can be provided to orient the tubular inserts 830, 840 and to maintain the width of the nozzles 835, 845. The standoffs 839 can also help maintain the width of the nozzle supply channel 1111, which is defined between the outer tubular body member 810, and the inner tubular insert members 830, 840. The nozzle supply channel is in fluid communication with each nozzle, and is supplied with pressurized insufflation gas from the insufflation plenum 837. Alternatively, if desired, multiple nozzle supply channels can be provided, each of which receive pressurized gas from the insufflation plenum 837, and supply respective nozzles with pressurized gas.

The nozzles 835, 845 form barriers to escape of gas from within the abdominal cavity 430, similarly to the above description, in connection with the embodiment of FIGS. 3-8. A pressure gradient is created and maintained by the nozzles 835, 845 of the trocar 800, between the pressure of the abdominal cavity 430 and that of the surrounding environment. As mentioned above, a plurality of nozzles create a plurality of pressure zones, limiting the burden on any one nozzle to create and maintain a large pressure differential. Such plurality of nozzles also provide redundancy, and therefore a better chance that a complete seal will be maintained around and between surgical instruments inserted through trocars in accordance with the invention. The number of nozzles can be as many as desired, so as to create a series of pressure differentials, to inhibit escape of pressure from the abdominal cavity 430. Such an end can be achieved by providing a plurality of inner tubular inserts, similar to that of insert 840, defining nozzles in-between each adjacent insert. In situations with a plurality of nozzles, it may be beneficial to provide nozzle supply channels with increasing cross-sectional area, to provide sufficient pressurized fluid to nozzles arranged nearer the distal end of the trocar.

An insufflation port 817 is provided and is in fluid communication with and supplies pressurized insufflation fluid to the insufflation plenum 837, and in-turn to the nozzle supply channel 1111 and the nozzles 835, 845 themselves.

Figure 10:
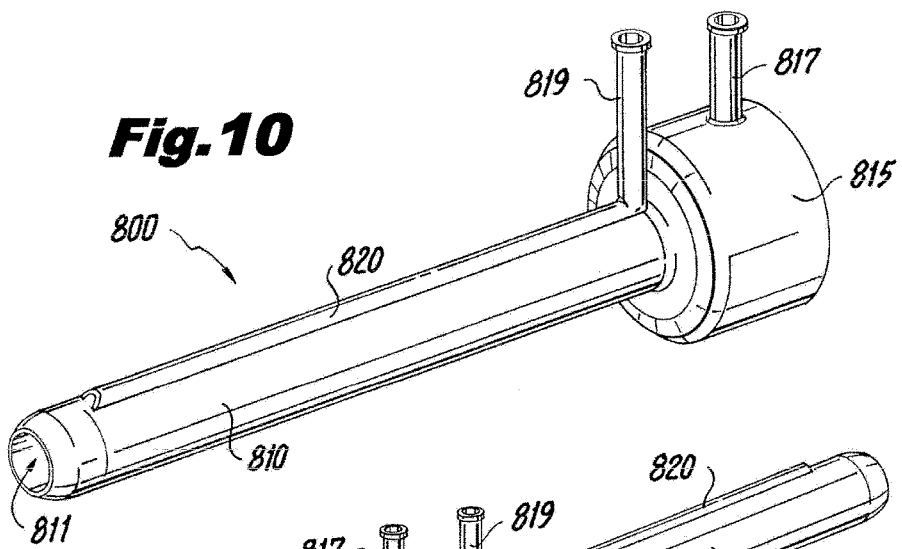
FIG. 10 is an isometric view from a distal end of a third embodiment of a trocar in accordance with the invention, wherein the trocar includes two fluid seal nozzles.
Figure 11:
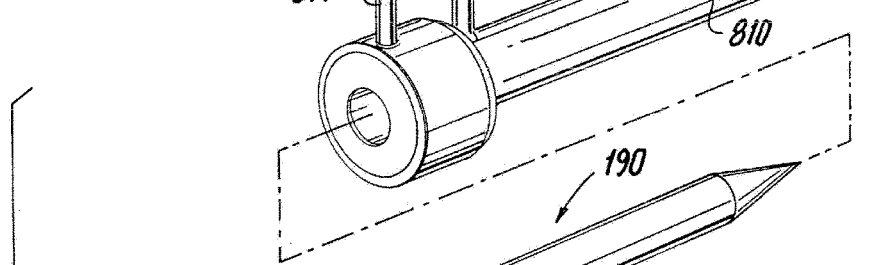
FIG. 11 is an isometric view from a proximal end of the embodiment of FIG. 10, illustrating the trocar and a removable inserter which, when inserted through the central lumen of the trocar, enables insertion of the trocar through the abdominal wall of a patient.
Figure 12:
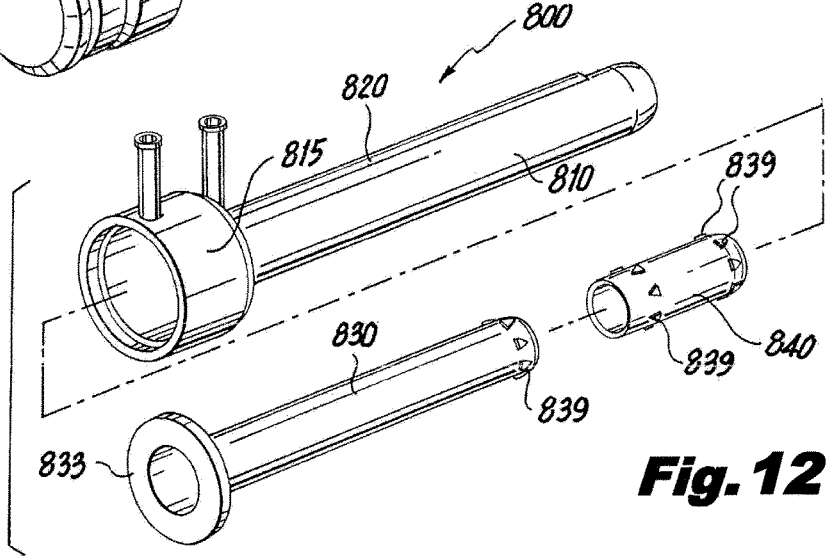
FIG. 12 is an exploded view of the embodiment of FIG. 10, illustrating inner and outer tubular members, which cooperate to form fluid channels and two fluid seal nozzles therebetween.

As best seen in FIG. 10, a pressure sense port 819 is provided on the trocar 800 of FIGS. 10-15. On one end, the port 819 interfaces with a pressure-monitoring element of the external system 550. The pressure sense port 819 transitions into a pressure-sense channel 1121 formed on the body member 810, which terminates in the distal end portion of the trocar 800, so that it can be exposed to the pressure within the abdominal cavity 430. Alternatively, the pressure sense channel 1121 can be formed within a wall of the body member 810. Alternatively still, as described below, the pressure sense member can even be a separate element.

With reference to FIGS. 16-20, another embodiment of a trocar constructed in accordance with the present invention is designated generally by reference numeral 1400. This trocar 1400 differs from the trocar 100 of FIGS. 3-8, in the placement of the pressure sense channel 1420, which is instead similar to that of the trocar 800 of FIGS. 10-15, in that it is disposed on an outside surface of the trocar body 1410.

Figure 16:
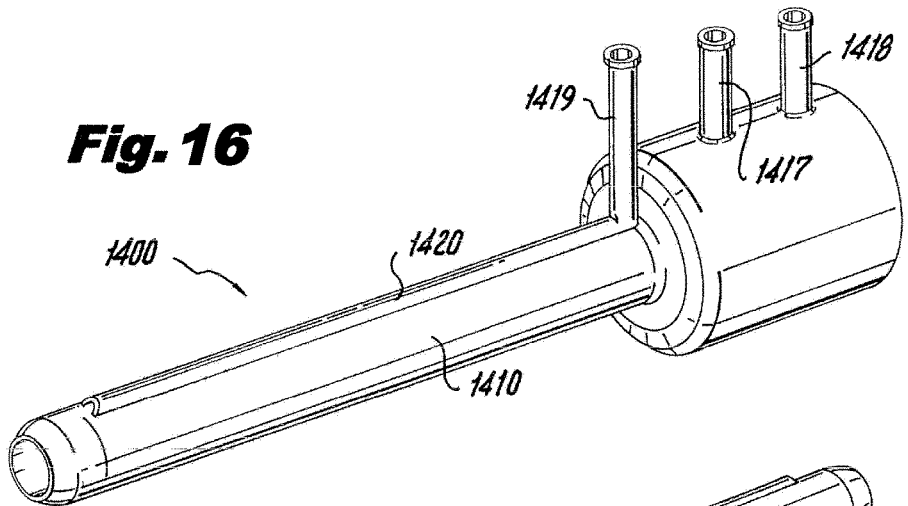
FIG. 16 is an isometric view from a distal end of a fourth embodiment of a trocar in accordance with the invention, wherein the trocar includes a proximally oriented pressure chamber.
Figure 17:
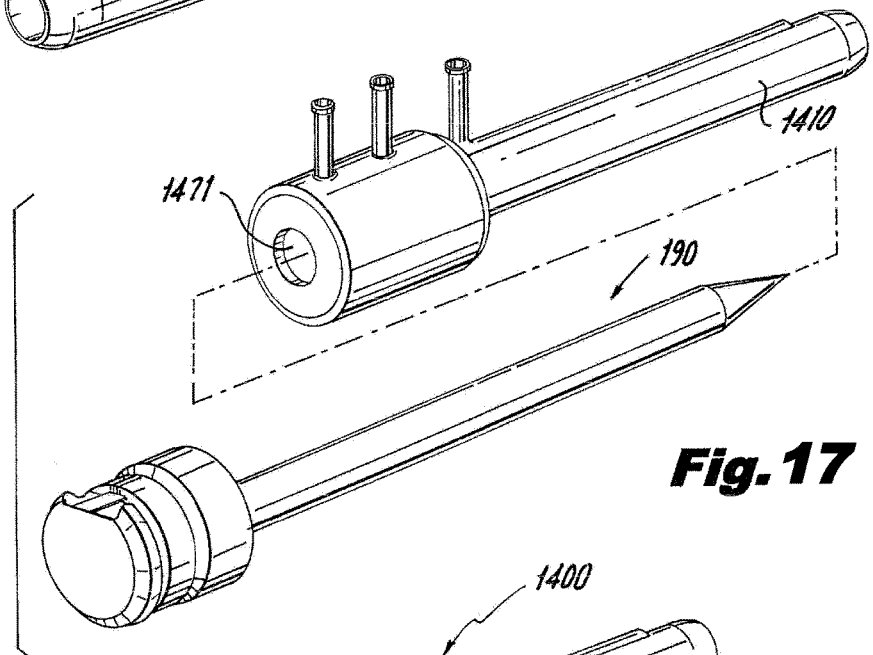
FIG. 17 is an isometric view from a proximal end of the embodiment of FIG. 16, illustrating the trocar and a removable inserter which, when inserted through the central lumen of the trocar, facilitates insertion of the trocar through the abdominal wall of a patient.
Figure 18:
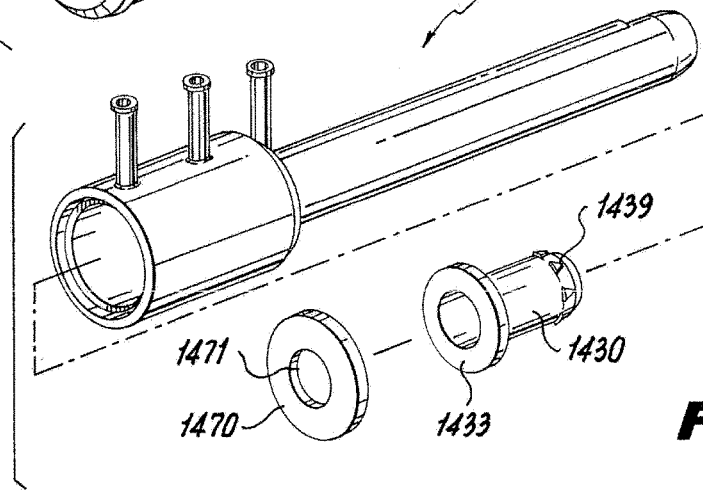
FIG. 18 is an exploded view of the embodiment of FIG. 16, illustrating an outer tubular member, and proximal insert members, which cooperate to form a fluid seal nozzle and a proximal pressure chamber, respectively.
Figure 21:
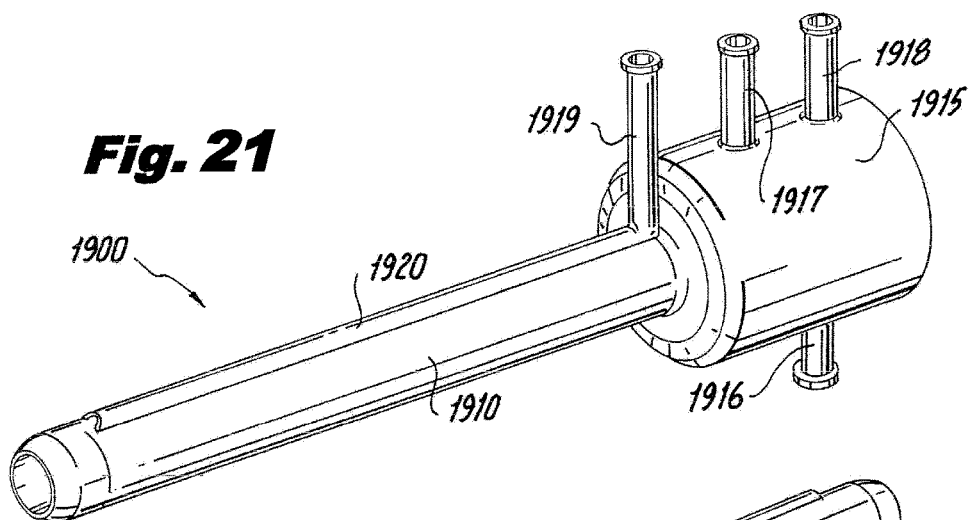
FIG. 21 is an isometric view from a distal end of a fifth embodiment of a trocar in accordance with the invention, wherein the trocar includes a proximally oriented pressure chamber with a recirculation capability.
Figure 22:
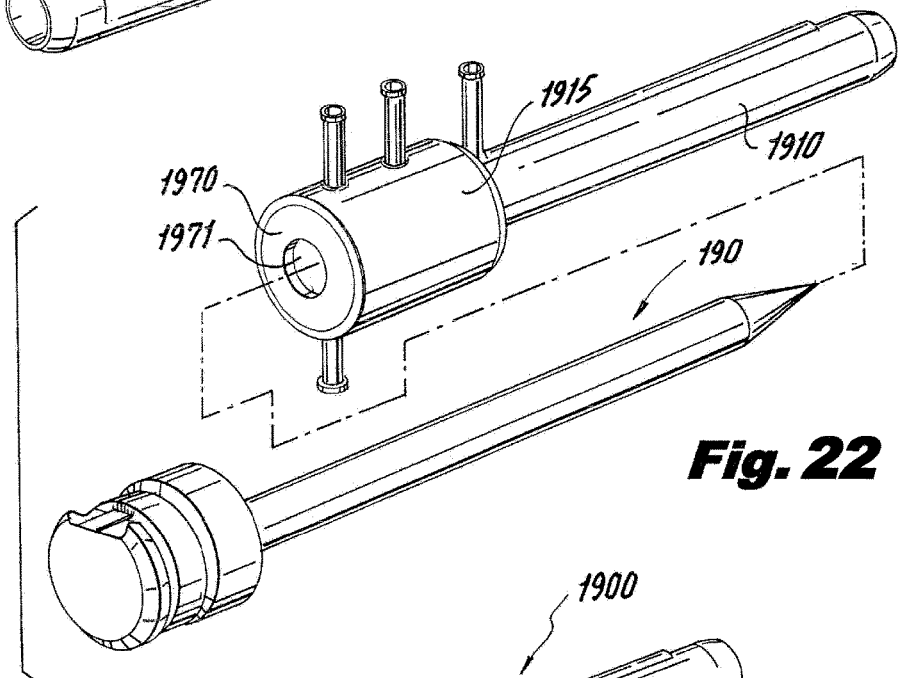
FIG. 22 is an isometric view from a proximal end of the embodiment of FIG. 21, illustrating the trocar and a removable inserter which, when inserted through the central lumen of the trocar, facilitates insertion of the trocar through the abdominal wall of a patient.
Figure 23:
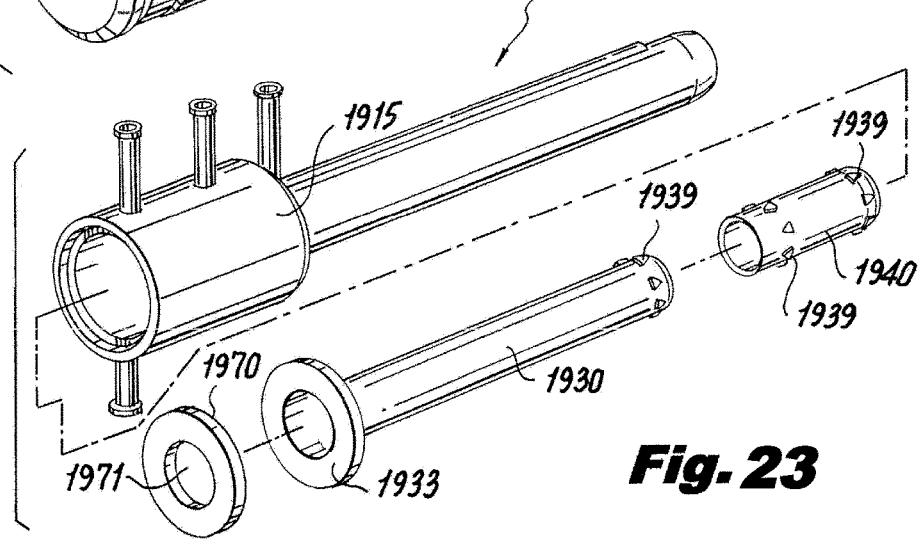
FIG. 23 is an exploded view of the embodiment of FIG. 21, illustrating an outer tubular member, and insert members, which cooperate to form two fluid seal nozzles and a proximal pressure chamber, respectively.

As best seen in FIGS. 16, 19 and 20, the pressure sense channel 1420 is in fluid communication with a pressure sense port 1419, provided on the trocar 1400. Naturally, a pressure sense channel similar to that of the trocar 100 of FIGS. 3-8 can be substituted. As also can be seen, an insufflation port 1417 is provided in the expanded diameter proximal portion 1415 of the trocar 1400, which connects to the insufflation plenum 1437, which in-turn provides pressurized insufflation fluid through a substantially annular nozzle supply channel 1811, to the nozzle 1445. The tubular insert member 1430 terminates at the nozzle 1445, and can include standoffs 1439, as set forth above. An inserter 190, can be provided, as with other embodiments described above and below.

With reference to FIG. 20, the trocar 1400 of FIGS. 16-20 includes a proximally arranged pressure chamber 1475. The chamber is defined within the expanded diameter portion 1415 of the trocar body 1410, and is bordered proximally by a reduction annulus 1470, with a central aperture 1471 defined therein to allow passage of surgical instruments and the like. The pressure chamber 1475 is bordered on a distal end by an expanded diameter portion 1433 of the tubular insert 1430, which insert 1430, helps define a nozzle 1445 at its distal end (See FIG. 19). The pressure chamber 1475 receives a flow of pressurized fluid from a pressure port 1418, which is supplied by the external system 550. The fluid supplied to the pressure chamber 1475 can be the insufflation gas, or alternatively, can be another gas. By creating a region of increased pressure in the chamber 1475, proximal egress of insufflation gas through the trocar, from the abdominal cavity 430 of the patient, can be reduced. While the pressurized fluid entering the chamber 1475 will ultimately be lost to the surrounding environment through the aperture 1471, a recovery and recycling facility can be provided, as will be described in connection with the embodiment of FIGS. 21-25, below.

Reference will now be made to FIGS. 21-25, which illustrate a further embodiment of a trocar constructed in accordance with the invention. This trocar 1900 is similar to the trocar 1400 of FIGS. 16-20, but includes a nozzle arrangement similar to the trocar 800 of FIGS. 10-15. Additionally, however, as best seen in FIG. 25, the pressure chamber 1975 includes a recovery port 1916 to enable removal and/or recirculation of gas that would otherwise exit through the proximal end of the trocar 1900.

The pressure sense channel 1920 is in fluid communication with a pressure sense port 1919, provided on the trocar 1900. As with any embodiment, a pressure sense channel similar to that of the trocar 100 of FIGS. 3-8 can be substituted in place of the pressure sense channel 1920. As also can be seen, an insufflation port 1917 is provided in the expanded diameter portion 1915 of the trocar 1900, which connects to the insufflation plenum 1937. The insufflation plenum 1937 in-turn provides pressurized insufflation fluid/ gas through a substantially annular nozzle supply channel 1911, to the nozzles 2235, 2245.

As can be seen, a tubular body member 1910 is provided, which includes an expanded diameter proximal end portion 1915 that houses the insufflation plenum 1937. As can be seen in FIG. 25, an expanded diameter end portion 1933 of the proximal insert member 1930 helps seal and define the insufflation chamber 1937 from the pressure chamber 1975, above. As best seen in FIGS. 24 and 25, two tubular insert members 1930, 1940 are provided. A lower, more distal nozzle 2245 is defined between an increased thickness portion 1901 of the body member 1910, and the most distal tubular insert 1940. A second, more proximal nozzle 2235, is defined between the proximal edge of the distal tubular insert 1940, and the distal edge of the proximal tubular insert 1930. As with any embodiment described herein, an inserter 190, can be provided to aid insertion through the abdominal wall 410 of a patient.

The proximally arranged pressure chamber 1975 is defined within the expanded diameter portion 1915 of the trocar body 1910, and is bordered proximally by a reduction annulus 1970, with a central aperture 1971 defined therein to allow passage of surgical instruments and the like. The pressure chamber 1975 is bordered on a distal end by an expanded diameter portion 1933 of the tubular insert 1930. The pressure chamber 1975 receives a flow of pressurized fluid from a pressure port 1918, which is supplied by the external system 550. The fluid supplied to the pressure chamber 1975 can be the insufflation gas, or alternatively, can be another gas. By creating a region of increased pressure in the chamber 1975, proximal egress of insufflation gas from the distal end of the trocar, and from the abdominal cavity 430 of the patient can be reduced.

The pressurized fluid entering the chamber 1975 will at least in-part, be collected and recycled through the recovery port 1916, and can be sent to a treatment device 2255, and recycled. The recovered fluid/gas can be treated to remove particulate matter, including smoke and/or liquids, can be humidified or dehumidified, heated or cooled, as desired. The recycled fluid can then be pressurized and sent back to the pressure port 1918, or can be re-inserted into a main supply, so that it can be used either for the pressure chamber 1975, or sent to the nozzle(s) 2235, 2245. Alternatively still, the recovered fluid can be discarded if desired. The collection and removal and/or recycling of recovered fluid/gas can accomplish certain desirable results. For example, if the fluid can be recycled, there is less waste, and therefore less expense for insufflation fluid/gas for each procedure. Even if the collected fluid is discarded, such fluid is still prevented from exiting the proximal end of the trocar, preventing such fluid from escaping into the environment untreated. This also helps prevent fluid from being ejected toward those in the operating room.

Moreover, the recovery port 1916 can recover liquids that may exit through the trocar. As the liquids exit the trocar, they are directed radially outwardly, toward the recovery port 1916. Also, although the recovery port 1916 is illustrated on an opposite side of the expanded diameter portion 1915, it can be arranged so that any tube would connect in the same region as the other three ports, to reduce encumbrance to a surgeon.

As with the foregoing embodiments, standoffs 1939 can be provided to orient the tubular inserts 1930, 1940 and to maintain the width of the nozzles 2235, 2245. The standoffs 1939 can also help maintain the width of the nozzle supply channel 1911, which is defined between the outer tubular body member 1910, and the inner tubular insert members 1930, 1940.

Reference will now be made to FIGS. 26-28, which illustrate yet another embodiment of a trocar in accordance with the present invention, which is designated generally by reference numeral 2400. This trocar 2400 includes a similar pressure channel 2421 to the trocar 100 illustrated in FIGS. 3-8. The pressure sense channel 2421 is defined between the outer tubular body member 2410 and a second, inner tubular body member 2420. The pressure sense channel 2421 is in fluid communication with a pressure sense plenum 2439, which in-turn is in fluid communication with a pressure sense port 2419. As can best be seen in FIG. 26, an insufflation port 2417 is provided in the expanded diameter proximal portion 2415 of the trocar 2400, which connects to the insufflation plenum 2437, which in-turn provides pressurized insufflation fluid to the nozzle 2645. The inner tubular member 2420 helps define the nozzle 2645 at its proximal end portion, in conjunction with a baffle insert 2430, which defines the upper limit of the nozzle 2645. Standoffs 2435, as set forth above, can be provided to maintain nozzle geometry.

As with the foregoing embodiments, the principle of operation of the nozzle 2645 is such that a region in which the force of gas entering from the nozzle 2645 at least equals that of the force of pressure within the abdominal cavity, acting within the channel 2401, or just beyond the channel 2401, in the abdominal cavity 430. A pressure gradient is created and maintained by the trocar 2400, between the pressure of the abdominal cavity 430 and that of the surrounding environment, such as an operating room.

As can best be seen in FIG. 28, the trocar 2400 additionally includes a proximally arranged baffle insert 2430, which aids in reducing noise created by the flow of insufflation gas in the trocar 2400. A sound-absorbent material 2438, such as a foam rubber, for example, can be used, and be inserted between separation portions 2433 of the insert 2430. The sound-absorbent material 2438 can be provided in cut halves, as illustrated, or in complete rings. Alternatively, the insert 2430 can be provided without additional sound absorbent material. The rigid portion of the insert 2430 can be a unitary component as illustrated, or can include multiple stacked elements, each of which engages adjacent stacked element. As illustrated in FIG. 29, the distal end of the insert 2430 can be provided with standoffs 2435, and helps define the nozzle 2645, in conjunction with a proximal nozzle surface 2427 of the inner tubular member 2420. Standoffs 2423 can additionally be provided between the inner tubular member 2420 and the outer tubular member 2410. Interior openings 2431 in the rigid portion 2430 can be provided, to enable the sound-absorbent material 2438 to absorb sound.

Further, a recovery means such as in the embodiment of FIGS. 21-25, can be configured in this embodiment, to aid collection of gas that would otherwise exit the trocar 2400.

Reference will now be made to FIGS. 30-37, which illustrate various embodiments of caps that can be secured to a proximal end of trocars, to help seal the trocars and prevent excessive loss of insufflation gas, and/or prevent contaminants from entering the lumen of the trocar and thus the abdominal cavity. A cap may be desirable since, in use, while a net loss of pressure in the abdominal cavity 430 is not experienced, some amount of insufflation gas typically will escape through the proximal aperture of the lumen of the trocar 2801. This effect is minimized by use of a gas recovery and recirculation system. However, use of a cap can be helpful under some circumstances. For example, if it is desired to reduce the flow of, or shut off the insufflation gas completely, then escape of fluid from the abdominal cavity 430 of the patient must be inhibited to maintain the pneumoperitoneum.

Figure 30:
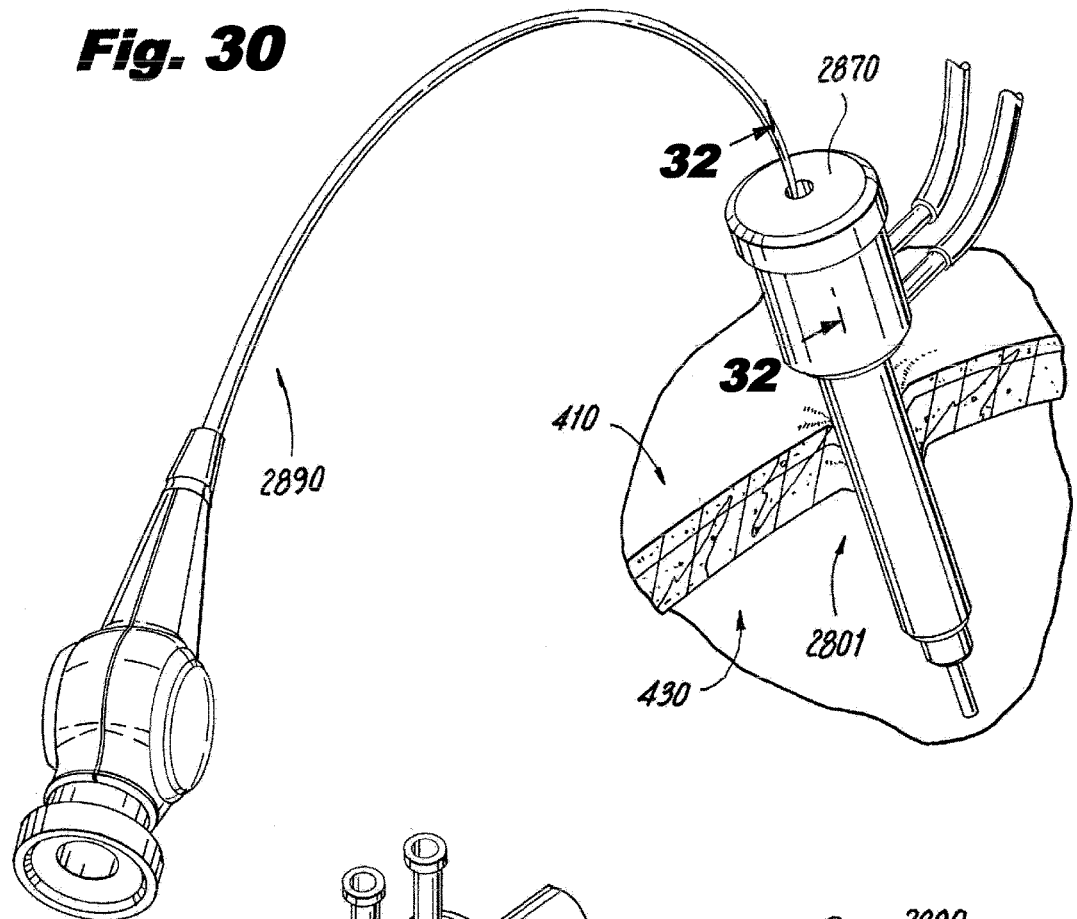
FIG. 30 is an environmental view illustrating a trocar in accordance with the invention, having a cap attached to the proximal end thereof. A surgical instrument is inserted through the cap and through the lumen of the trocar, into the abdominal cavity of the patient.
Figure 31:
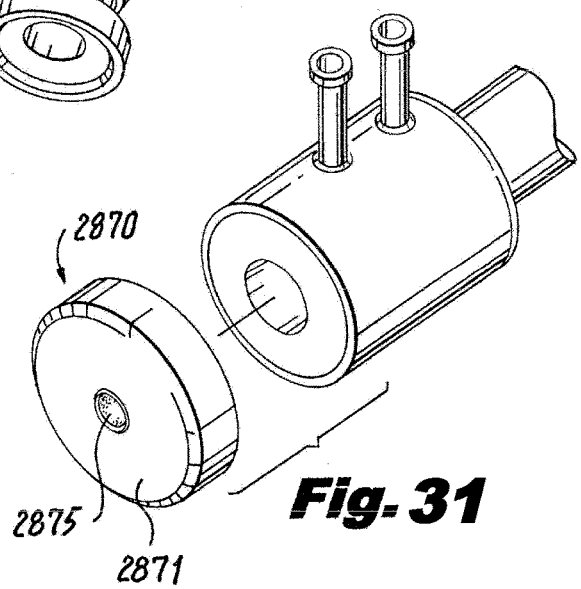
FIG. 31 is an exploded view of the cap and trocar of FIG. 30.
Figure 32:
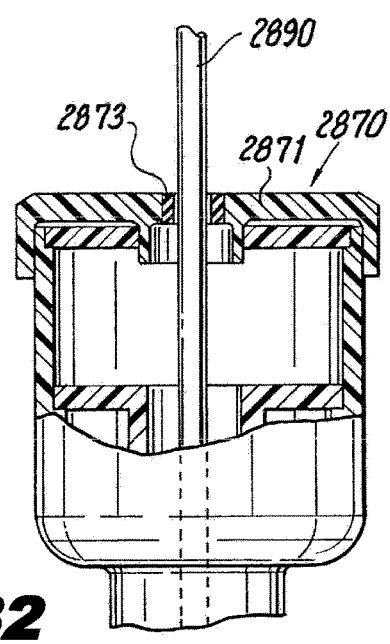
FIG. 32 is a partial cross-sectional view of the cap and trocar of FIG. 30, with the surgical instrument inserted therethrough.

The cap 2870 of FIGS. 30-32 includes a central aperture 2875, surrounded by a resilient ring of material 2873, which can compress and help seal the junction between the rigid body portion 2871 of the cap 2870 and a surgical instrument 2890, when inserted into the aperture 2875. This cap and other caps described herein can be joined to the proximal end of the trocar 2801 by any suitable means, including but not limited to a latching element, snap fit, friction fit, adhesive or mechanical fasteners, such as hook-and-loop fasteners.

Figure 33:
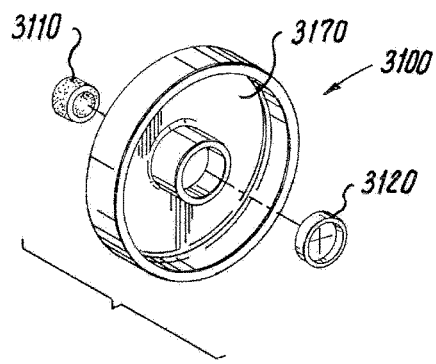
FIG. 33 is an exploded view of a cap in accordance with the invention, wherein the cap includes a valve and a secondary sealing element to seal between a surgical instrument and the cap body.

Referring to FIG. 33, which illustrates a cap constructed in accordance with the invention, which includes a main body portion 3170, a quadricuspid valve element 3120 having four cusps separated by slits, and a resilient ring element 3110 that enhances the sealing of the cap when an instrument is inserted therethrough. Naturally, the valve element 3120 can include more or less cusps, e.g., 2, 3 or 5.

Figure 34:
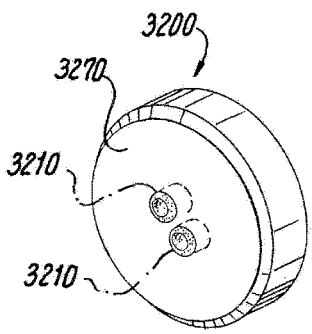
FIG. 34 is an isometric view of a further embodiment of a cap in accordance with the invention. The cap includes two apertures for sealable insertion of two instruments.

Referring to FIG. 34, the cap illustrated therein is designated generally with reference number 3200. The cap 3200 includes two apertures 3210, and a main body portion 3270. The apertures 3210 can enable sealed insertion of two separate instruments. Naturally, three or more apertures 3210 can alternatively be provided. The apertures 3210 can be provided with resilient inserts or portions and/or with a valve portion, such as valve 3120 shown in the embodiment of FIG. 31.

Figure 35:
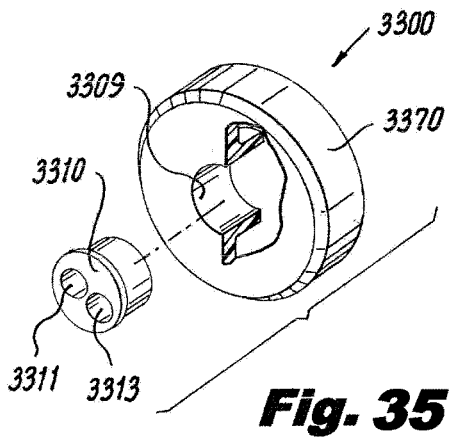
FIG. 35 illustrates a cap having a main aperture, which accepts a plug having a plurality of apertures formed therein, so that a user can select the size of aperture to use.

With reference to FIG. 35, the cap 3300 includes a main body portion 3370, and a plug 3310, which in-turn has two apertures 3311, 3313 formed therein. The plug 3310 can be inserted into the main body portion 3370 to enable use of two relatively small-diameter surgical instruments. The plug 3310 can be removed to enable insertion of a larger-diameter instrument, or for other reasons, depending on the particular situation.

Figure 36:
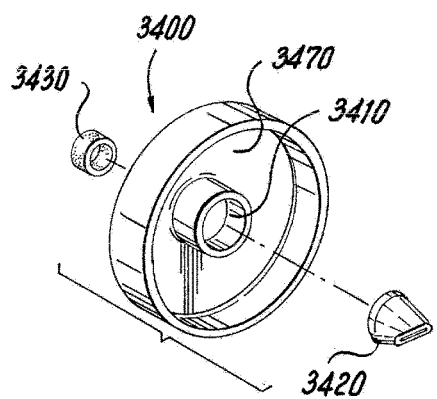
FIG. 36 is an exploded view of a cap having a duckbill-type valve and a secondary sealing element to seal between a surgical instrument and the cap body.

As shown in FIG. 36, the cap 3400 includes a duckbill-type valve element 3420, which is inserted into a receiving aperture 3410. A resilient ring 3430 can further be provided to additionally enhance sealing between an instrument and the cap body 340, when an instrument is inserted therethrough. This may be desirable, since when the duckbill valve 3420 is opened, and a round instrument is inserted therethrough, the duckbill valve might not completely seal around such instrument.

Figure 37:
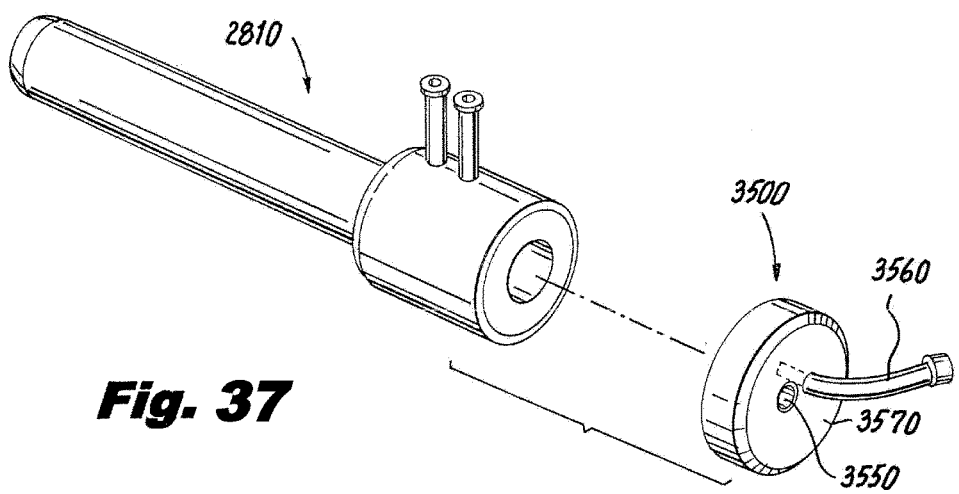
FIG. 37 illustrates a trocar in accordance with the invention, and a cap for insertion thereon. The cap includes a pressure sense line incorporated therewith to enable sensing of pressure within the abdominal cavity of the patient.

FIG. 37 illustrates a cap 3500, which includes an aperture 3550, a main body portion 3570, and a pressure sense line 3560. The pressure sense line can terminate in or near the cap body 3570 itself, or can extend through the lumen of the trocar 2810 to sense pressure within the abdominal cavity 430.

Figure 38A:
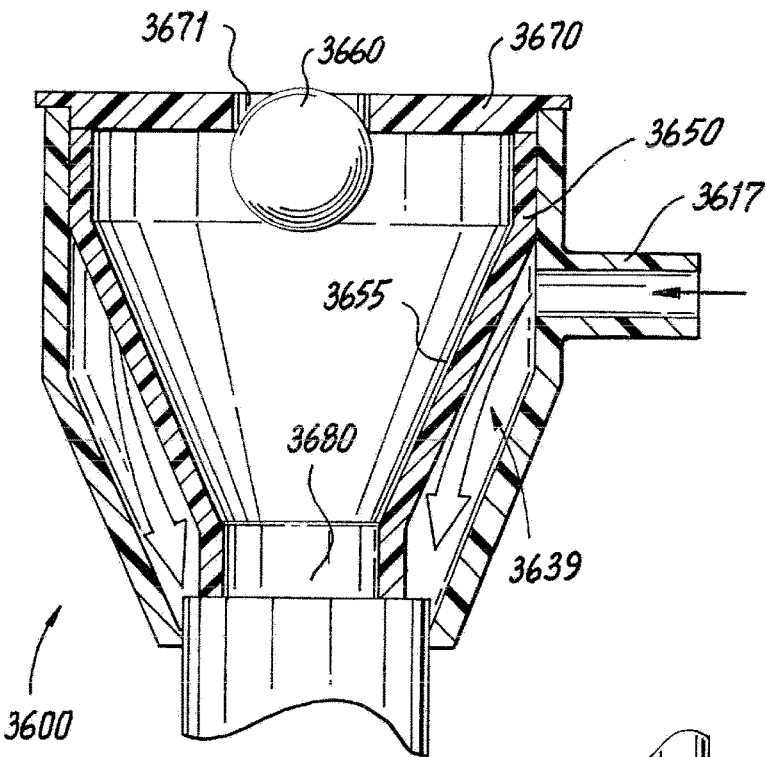
FIG. 38a illustrates a proximal ball valve for use in conjunction with trocars in accordance with the invention. The ball occludes a proximal aperture of the ball chamber due to a pressure differential between the chamber and the surrounding environment.
Figure 38B:
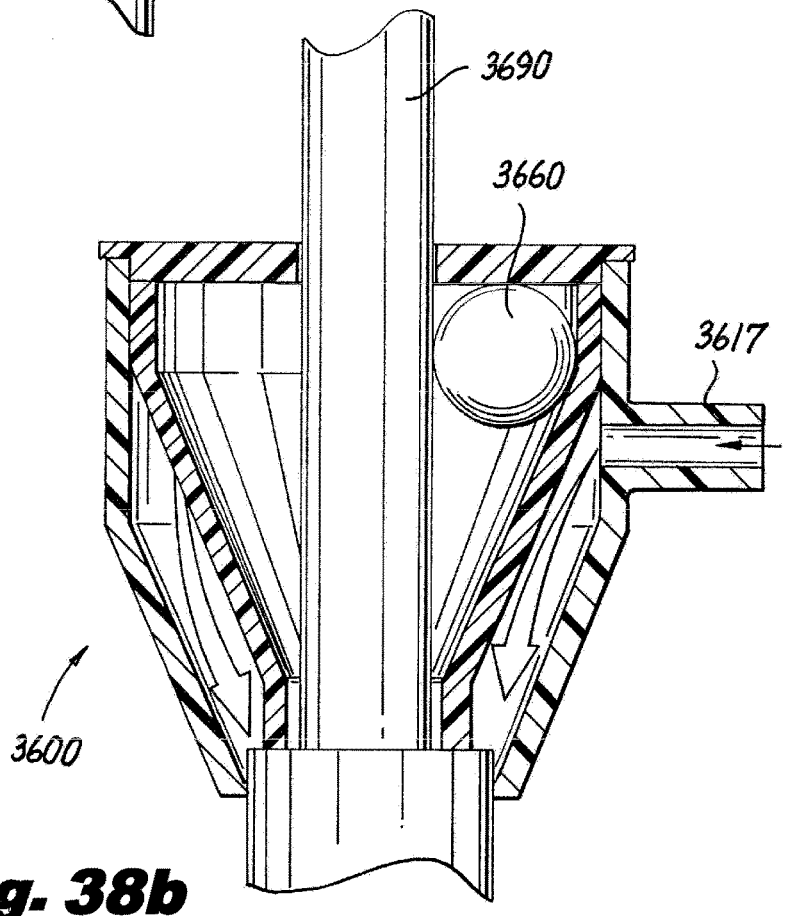
FIG. 38b illustrates the ball valve of FIG. 38a, with a surgical instrument inserted therethrough. The surgical instrument urges the ball away from the aperture, allowing the instrument access to the lumen of the trocar attached thereto.

FIGS. 38*a* and 38*b* illustrate a trocar end 3600 having a ball valve arranged at the proximal end portion thereof. The substantially spherical valve member or "ball" 3660 is housed within a ball chamber 3650 and capable of closing off a proximal aperture 3571. The ball 3660 can be urged into place by a difference in pressure between the ball chamber 3650, trocar lumen, and abdominal cavity of a patent, with which it is in fluid communication. As shown in FIG. 38*b*, when an instrument 3690 is inserted through the aperture 3671, the ball 3660 is urged toward the outer circumference of the chamber 3650, until the instrument 3690 is removed. As can be seen, an insufflation port 3617 and insufflation plenum 3639 can be easily accommodated alongside the ball valve chamber 3650.

Figure 39A:
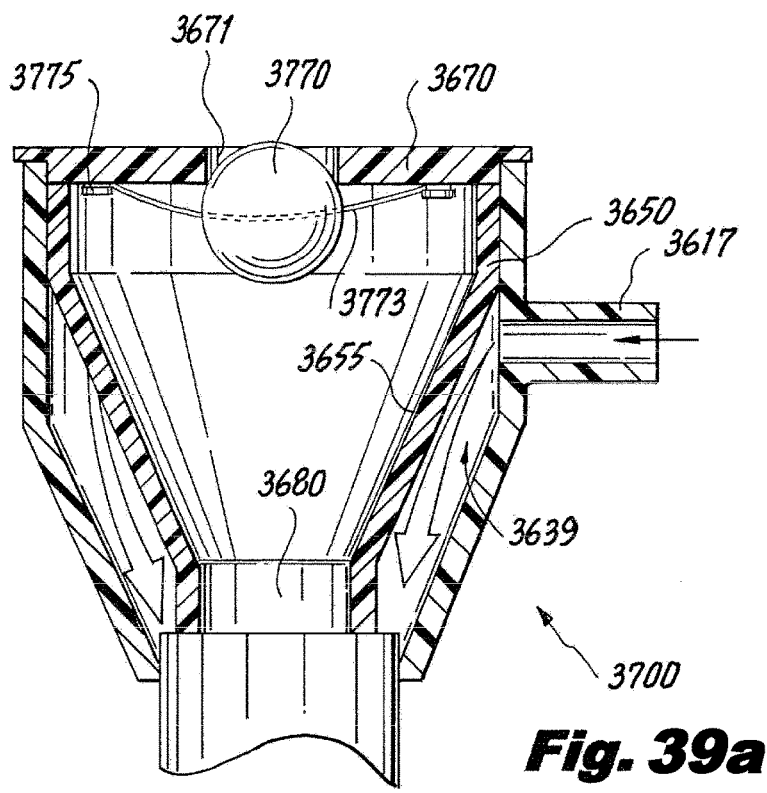
FIG. 39a illustrates a ball valve for use in sealing trocars in accordance with the invention. The ball is attached with one or more tethers to a proximal end wall of its housing, so that the tethers maintain a seal.

As shown in FIG. 39a, the ball 3770 can be resiliently tethered to a proximal portion of the interior wall 3655 of the ball chamber 3650. For example, a tether 3773 can be attached at or near the outer circumference of the proximal end of the ball chamber 3650. As illustrated, a single tether 3773 passes through the ball 2770, and is attached to posts 3775, although any suitable connection method can be used. The ball 3770 is preferably secured to the tether 3773, so that the ball 3770 can reliably seal the centrally located aperture 3671. When an instrument, such as instrument 3690, is inserted into the chamber, the ball 3770 will move to one side, stretching the tether(s) 3773 as needed. When the instrument is removed, the ball 3770 will revert to its initial position.

Figure 39B:
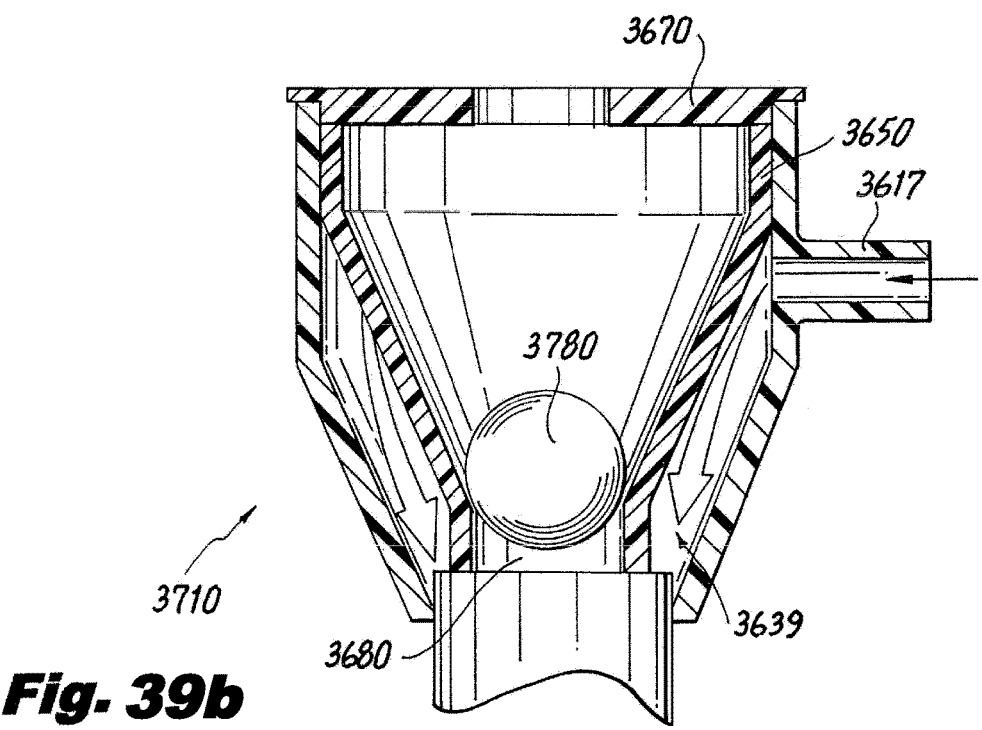
FIG. 39b illustrates a ball valve for use in sealing trocars in accordance with the invention. The ball has a mass such that it is capable of sealing the trocar when oriented in an upright position.

As shown in FIG. 39b, a valve can alternatively be provided having a ball 3780 with sufficient mass so that the ball 3780 can effectively occlude the lumen 3680 of the trocar simply by laying over the opening thereto. When a surgeon wishes to insert an instrument, such as instrument 3690, the surgeon need only slightly tilt the trocar to move the ball 3780 aside, and expose the lumen 3680 of the trocar. It is to be understood that such ball valves can be incorporated into any of the foregoing embodiments to provide additional encumbrance to loss of insufflation gas. Moreover, such ball valves can be provided in a separate cap, for attachment to a proximal end of the trocar. Of course, such ball valves can be provided, which can be universally utilized with any trocar, not only those described herein. Additional embodiments of ball valves in accordance with the invention are set forth hereinbelow in connection with FIGS. 48-51.

Figure 40:
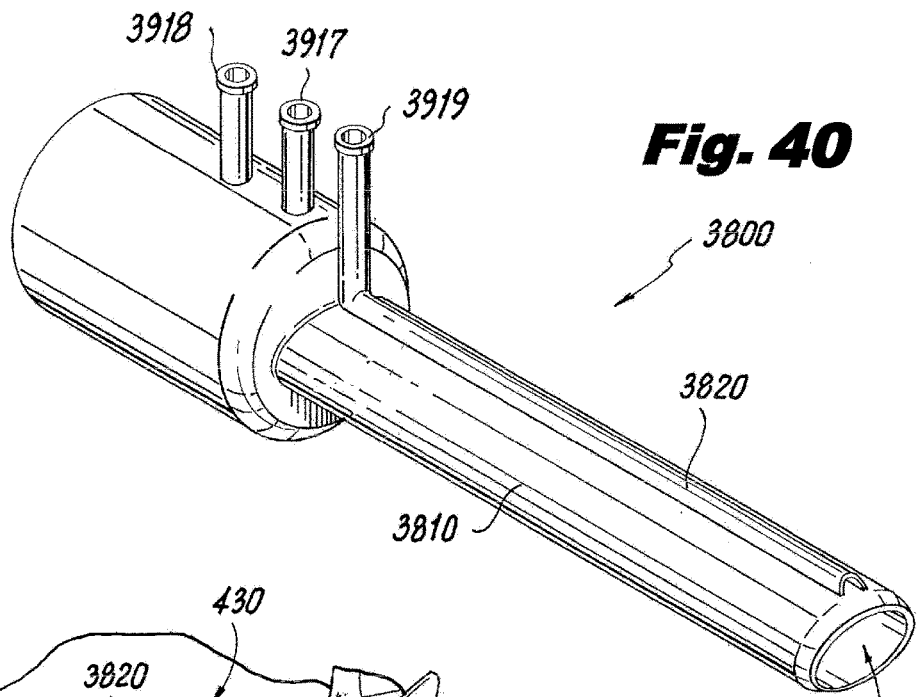
FIG. 40 illustrates a seventh embodiment of a trocar in accordance with the invention, where the trocar includes a substantially elliptical shape. A pressure sense channel is defined on the outer wall of the trocar.
Figure 41:
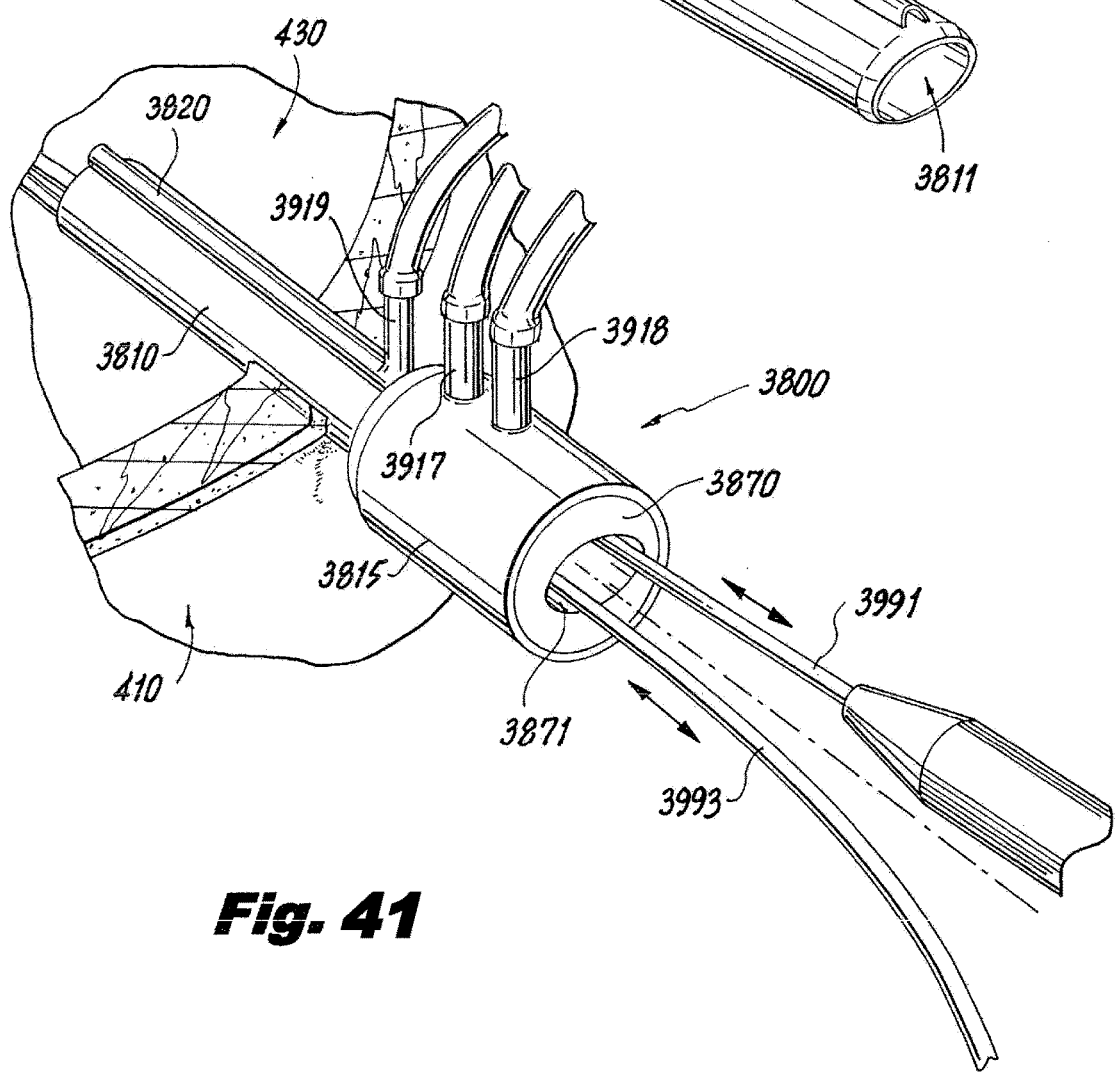
FIG. 41 is an operational, partial cross-sectional view of the trocar of FIG. 40, illustrating the trocar in use, inserted through an abdominal wall of a patient, having a plurality of surgical instruments inserted therethrough.

FIGS. 40-41 illustrate a trocar 3800 in accordance with the invention, having a generally elliptical cross-sectional shape. With the exception of the elliptical shape, the trocar 3800 is similar to the trocar 1400 of FIGS. 16-20. The trocar 3800 includes a proximally arranged pressure chamber (not shown). The chamber is defined within the expanded diameter portion 3815 of the trocar body 3810, and is bordered proximally by a reduction annulus 3870, with a central aperture 3871 defined therein to allow passage of surgical instruments 3991, 3993 and the like. The elliptical shape of the inner and outer surfaces also enables easier introduction of multiple surgical instruments. The pressure chamber receives a flow of pressurized fluid from a pressure port 3918, which is supplied by an external system. A recovery and recycling capability can be provided, as in the above embodiments. An insufflation port 3917 provides pressurized insufflation gas to the trocar 3800, and a pressure sense port 3919 interfaces with a pressure sense conduit 3820.

Figure 42:
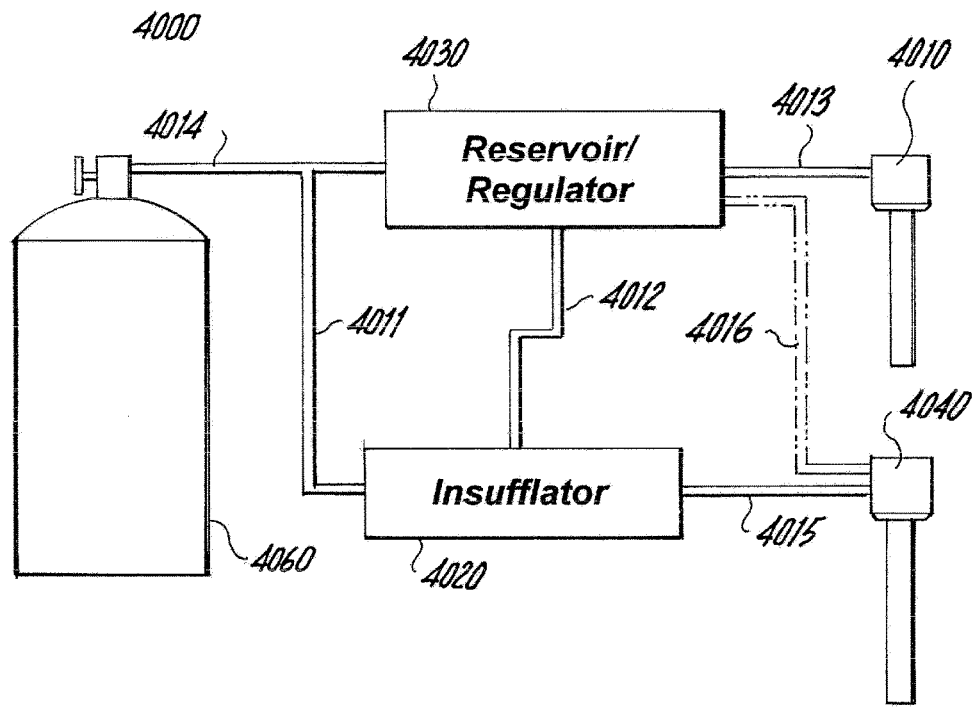
FIG. 42 illustrates an example system in accordance with the invention. The system includes a gas supply, an insufflator, and a pressure reservoir and regulator. The system is connected to two trocars, one of which includes a pressure sense capability incorporated therein, and which is connected to a pressure sense line connected to the insufflator.
Figure 43:
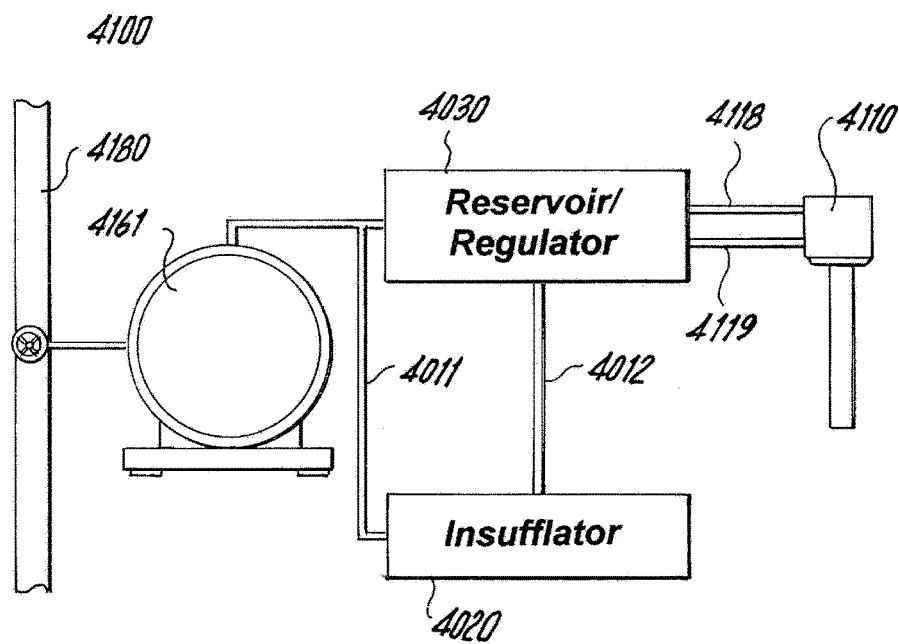
FIG. 43 illustrates another example embodiment of a system in accordance with the invention. The system includes a gas supply, an insufflator, and a pressure reservoir and regulator. The system is connected to a single trocar, which includes a pressure sense line incorporated therein, which is connected to the regulator portion of the system via a pressure sense line.

Systems in accordance with the invention include one or more of the trocars described hereinabove. FIGS. 42 and 43 illustrate system elements in accordance with the invention. A gas supply 4060 or a compressor 4161 are connected to and supply each system 4000, 4100, respectively, with insufflation gas, such as carbon dioxide, helium or xenon gas. The compressor 4161 can pressurize insufflation gas provided through a central hospital distribution system 4180, from gas cylinders 4060 or filtered air from the surrounding environment, the latter being potentially useful for gas that will not come into direct contact with the patient, such as for providing pressurized fluid to the chamber 1975 of FIG. 25. Pressure sensing means for measuring a pressure inside a body cavity can be provided in a diaphragm type valve, as illustrated in FIG. 9, by an electronic pressure transducer, or alternatively, by utilizing the pressure sensing capability of a surgical insufflator.

A pressure reservoir 4030 can be provided for maintaining a constant output pressure to the insufflation trocar. The pressure reservoir can simply be a closed volume where pressure builds by compressing fluid held therein, or can be a pressure accumulator that mechanically stores received pressure until it is needed, such as by compression of a spring-loaded diaphragm. Alternatively still, the pressure reservoir can include an active compression means, such as a compressor, to set fluid within the reservoir to the desired pressure. Since typical surgical insufflators cycle between pressurizing and pressure sensing modes, a reservoir can be used to even out the supply of pressurized fluid, so the fluid seals in the trocar are not starved of pressurized fluid, and don't allow the abdominal cavity of the patient to lose pressure.

A pressure regulating means, for regulating pressure output to the trocar can be provided, and can be embodied in a diaphragm type valve 700, as illustrated in FIG. 9, or alternatively can be an electromechanical device, which is controlled by a computer controller to set a valve so that an appropriate pressure is released into the trocar 4010 by way of conduit 4013. Alternatively, the pressurization means and pressure sensing means can both be provided in a surgical insufflator 4020. Alternatively still, the pressurization means can be a separate compressor.

The pressure regulating means can include a control element for setting by a user to select a desired pressure for the surgical cavity and/or output to the seal nozzles, and an electromechanical flow-control valve for adjusting a flow of insufflation gas to maintain the desired pressure within the surgical cavity. Moreover, the pressure regulating means can be a two-stage pressure regulator, capable of simultaneously regulating output at two set pressures. Alternatively or additionally, such pressure regulator can include variable-output capability, to allow control of the output pressure(s), based on a control signal.

FIG. 42 illustrates a first trocar 4010, which is used for insufflation and is connected by an insufflation conduit 4013 to the reservoir and regulator 4030. A second trocar 4040, which is used to sense pressure within the abdominal cavity of a patient, is connected to the insufflator via a pressure sense conduit 4015 connected between the second trocar 4040 and the insufflator 4020. The second trocar 4040 need only be a needle to sense pressure, but alternatively can be, itself, an insufflation trocar. If the second trocar is also an insufflation trocar, then a supply conduit 4016 is also provided to the second trocar 4040 from the reservoir/regulator. Since in this embodiment, use of a second insufflation trocar is optional, the pressure supply conduit 4016 is provided in phantom line.

The insufflator 4020, in accordance with the embodiment of FIG. 42, receives insufflation gas from the supply 4060 by a conduit 4011, and provides pressurized fluid to the reservoir 4030 by way of another conduit 4012. Since typical surgical insufflators operate using a pulsed supply, separated by periods of pressure sensing, the reservoir 4030, advantageously provides a constant fluid flow, even when in insufflator has paused to take a pressure measurement.

The embodiment of system 4100 of FIG. 43 differs from the system 4000 of FIG. 42, in that a pressure sense conduit 4119 and a insufflation conduit 4118 are both connected to a single trocar 4110. Further, a compressor 4161 is provided rather than simply a canister 4060 of gas, as in the embodiment of FIG. 40. Optionally, filtered ambient air can be used for the purpose of insufflation. However, more likely, the pressure of gas from a central gas supply 4180, which typically deliver gas at relatively low pressures, can be increased to the required pressure to form and create a fluid seal between the operative pneumoperitoneum and the surrounding environment.

Further, treatment devices can be provided to treat fresh or recirculated insufflation gas. Such treatment elements can include filtration elements, desiccating elements, such as a dryer, temperature control elements, such as heaters or coolers, or any other elements necessary to properly condition the insufflation gas.

Figure 44:
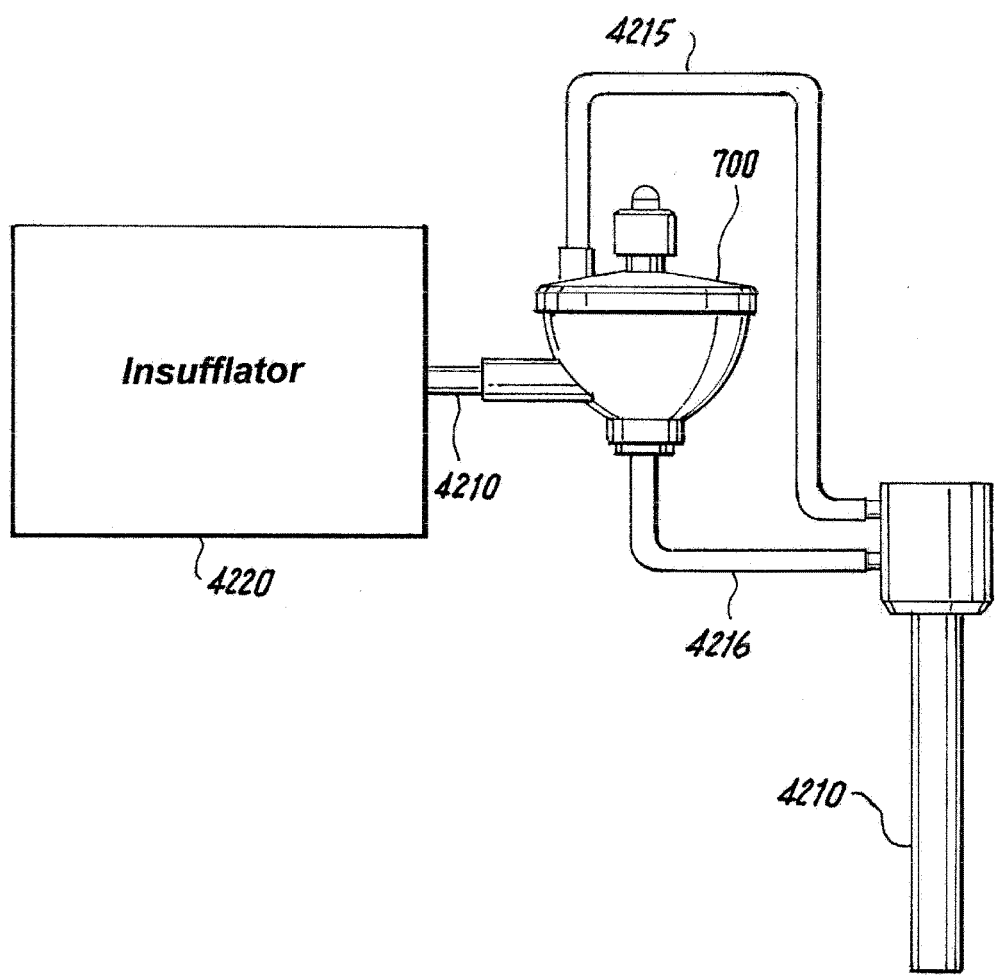
FIG. 44 illustrates a further system in accordance with the invention, where an insufflator provides pressure through a diaphragm valve to an insufflation trocar. A pressure sense line is connected to the diaphragm valve and the trocar to control flow of insufflation gas to the trocar.

With reference to FIG. 44, a further system in accordance with the invention is illustrated in which an insufflator 4220 provides pressure through a conduit 4217 to a diaphragm valve 700 (See FIGS. 9a-9c). The diaphragm valve 700, which can alternatively be a different device serving the same function, controls flow therethrough, and into another conduit 4216 to an insufflation trocar 4210. A pressure sense line 4215 is connected to the diaphragm valve 700 as well as to the trocar 4210 in order to control flow of insufflation gas to the trocar 4210.

Figure 45:
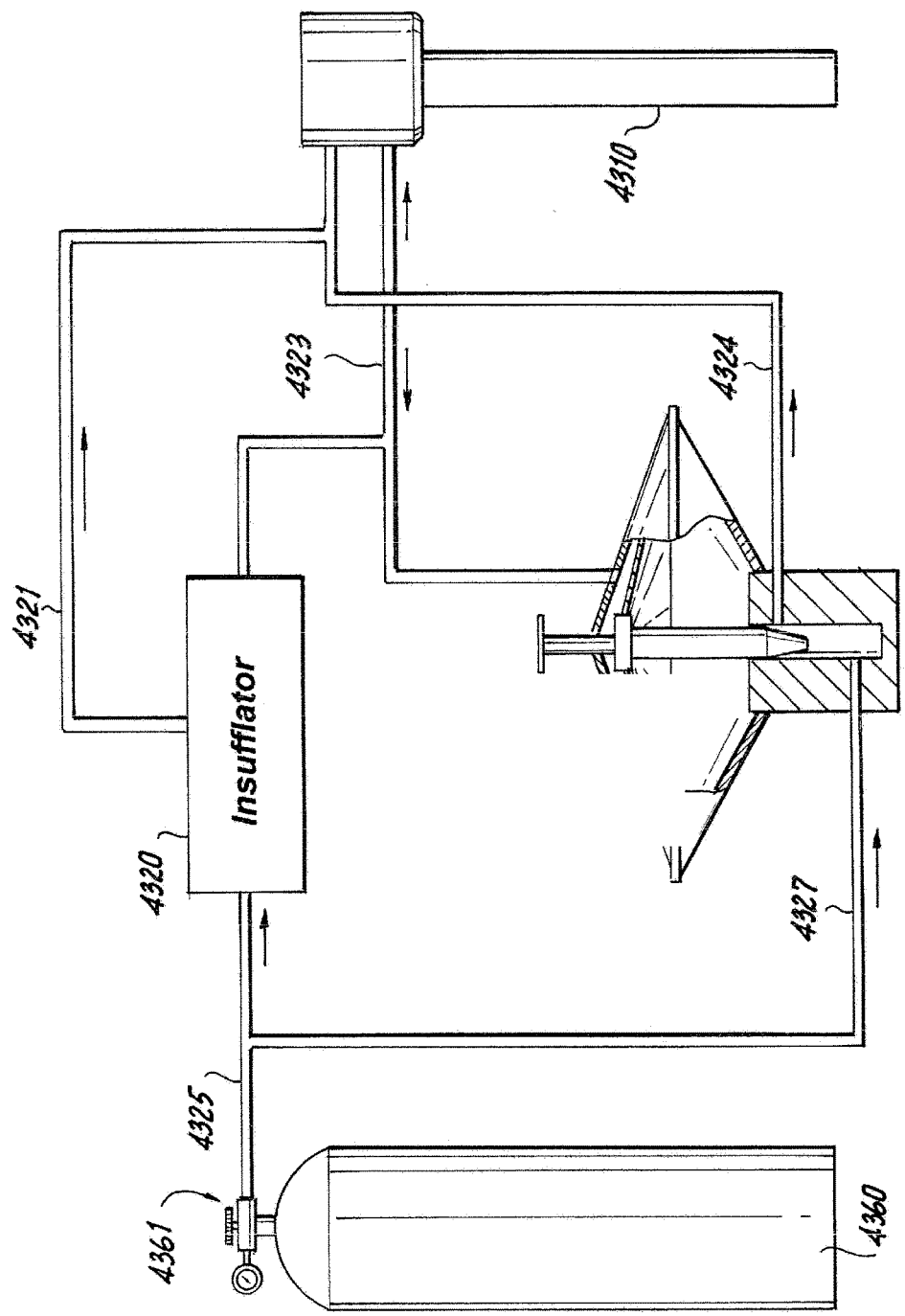
FIG. 45 illustrates still another system in accordance with the invention, with a diaphragm valve and surgical insufflator arranged in parallel.

FIG. 45 illustrates still another system in accordance with the invention, with a diaphragm valve 4330 and surgical insufflator 4320 arranged in parallel. Fluid is supplied from the cylinder or "bottle" 4360, through a regulating valve 4361 into supply conduits 4325 and 4327. Gas is supplied to the insufflator 4320, which pressurizes the insufflation fluid and outputs pressurized insufflation fluid through conduit 4321 to the trocar 4310. In parallel, fluid is supplied through a conduit 4327 to the diaphragm valve, which is controlled, as set forth hereinabove. Fluid is then output through conduit 4324 to the trocar 4310. The diaphragm valve 4330 is controlled through a common pressure sense channel 4323, shared with that of the insufflator.

Figure 46:
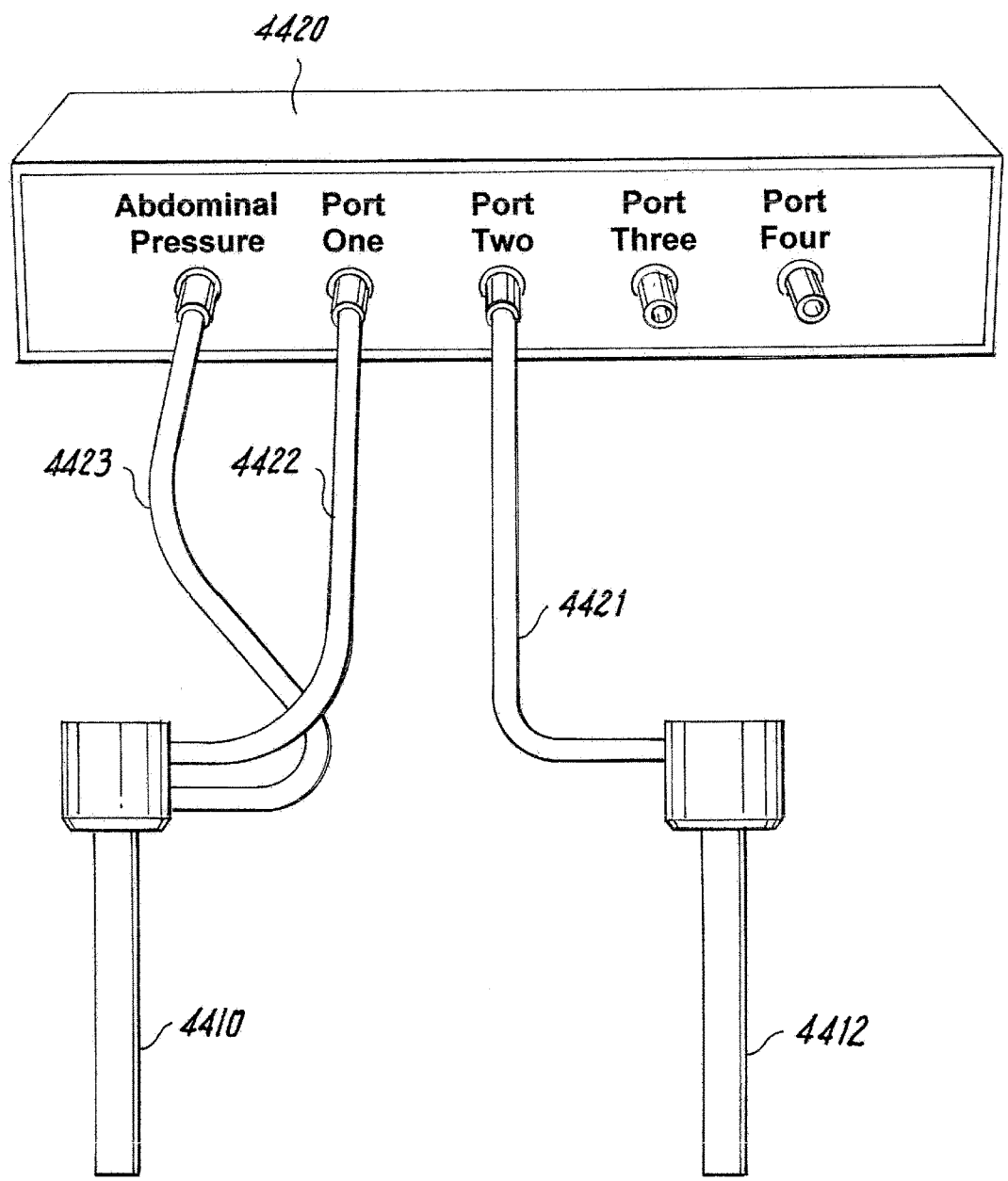
FIG. 46 illustrates one connection setup, including three tubes connecting trocars in accordance with the invention to a single control unit.
Figure 47:
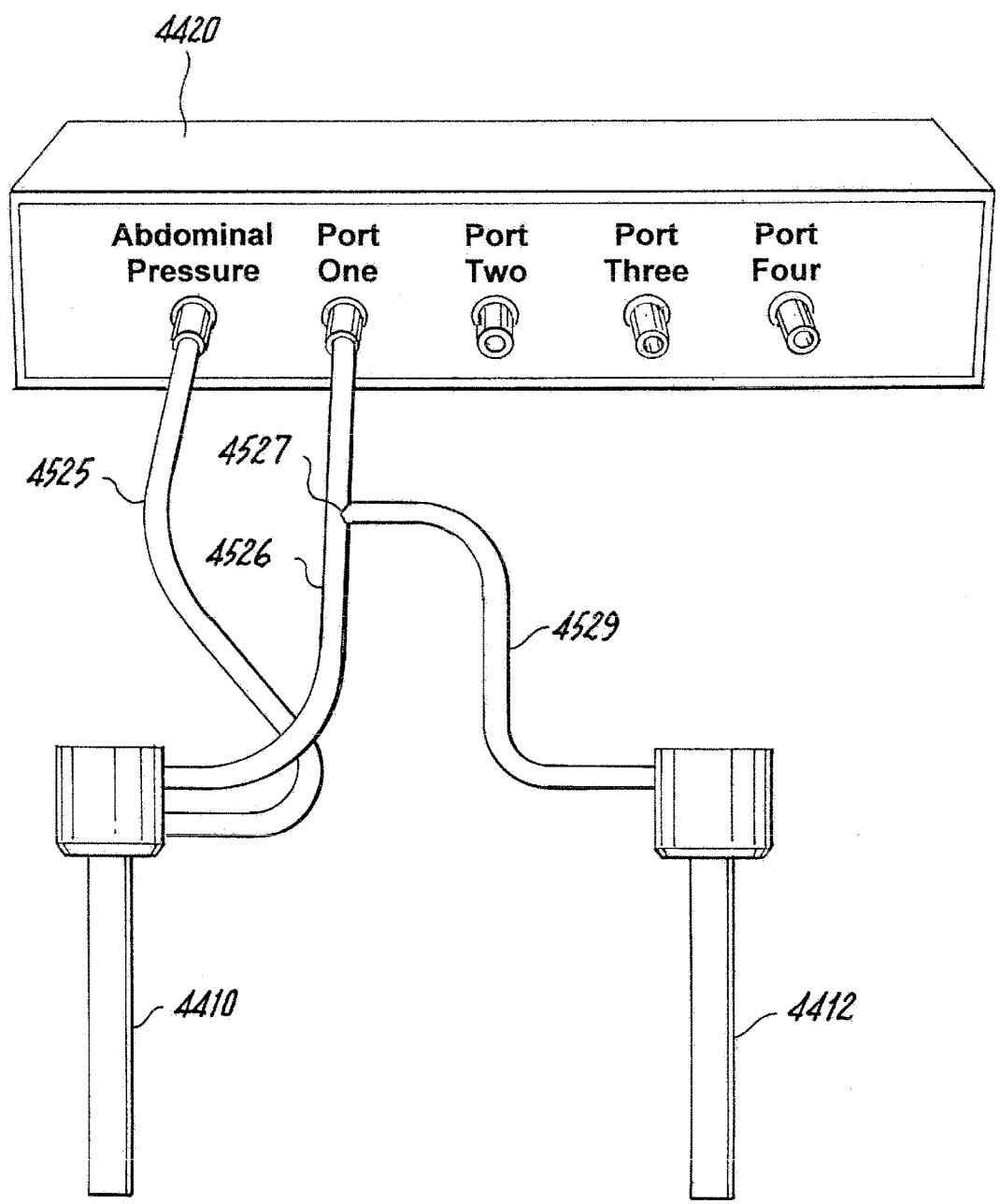
FIG. 47 illustrates another connection setup, including two tubes, one of which is bifurcated to supply pressurized fluid to two trocars in accordance with the invention.

FIG. 46 illustrates a connection setups, including three tubes 4421-4423, connecting trocars 4410, 4412 in accordance with the invention to a single control unit 4420. FIG. 47 illustrates another connection setup, including two tubes 4525, 4526, one of which (tube 4526) is bifurcated at point 4527, to supply pressurized fluid to two trocars 4410, 4412 in accordance with the invention. As can be seen, the setup of FIG. 47 utilizes one fewer port, due to the use of a bifurcated tube 4526. If desired, additional trocars can be added by connection to additional ports and/or through use of additional bifurcated tubes.

Also in accordance with the invention, a method is provided of sealing a pressurized cavity of a patient to enable a surgical procedure. The method includes providing one or more trocars in accordance with the invention, inserting the trocar(s) into the patient, connecting the trocar(s) to a supply of pressurized fluid, and supplying a flow of pressurized fluid to the trocar, which can include actuating a system in accordance with the invention. The method can further include inserting a surgical instrument through the lumen of the trocar, whereby the pressurized fluid supplied to the trocar forms a seal around the surgical instrument. Accordingly, loss of pressure is prevented from within the cavity of the patient. This and other methods in accordance with the invention can further include inserting a second surgical instrument through the lumen of the trocar, wherein the pressurized fluid supplied to the trocar seals around, and between, first and second surgical instruments, preventing loss of pressure from the cavity of the patient. This and other methods in accordance with the invention can further include removing one or more instruments from the lumen of the trocar. Such methods can also include providing one or more caps in accordance with the invention, so as to seal off proximal ends of the trocar(s).

Another method in accordance with the invention includes providing a trocar, supplying a pressurized fluid stream to the trocar and inserting a surgical instrument through a lumen of the trocar. The trocar has means to direct a stream of fluid through a lumen of the trocar to prevent loss of pressure within the cavity of the patient, due to loss of insufflation fluid past a surgical instrument inserted therethrough. The pressurized fluid supplied to the trocar can seal around the surgical instrument, preventing loss of pressure within the cavity of the patient. The means to direct a stream of fluid can include at least a first nozzle arranged in a proximal end portion of the trocar. The means to direct a stream of fluid can include at least a first nozzle arranged in a proximal end portion of the trocar and a second nozzle arranged in the trocar, axially spaced from the first nozzle. The means to direct a stream of fluid can additionally or alternatively include at least one nozzle which extends substantially circumferentially about the lumen of the trocar. Naturally, the immediately foregoing method can further include steps discussed in connection with the immediately preceding method and vice versa.

It will be apparent to those skilled in the art that various modifications and variations can be made in the device and method of the present invention without departing from the spirit or scope of the invention. Thus, it is intended that the present invention include modifications and variations that are within the scope of the appended claims and their equivalents.

What is claimed is:

1. A trocar assembly comprising:
 a) an elongated outer tubular member having opposed proximal and distal end portions and having a longitudinal axis extending therethrough;
 b) an elongated inner tubular member having opposed proximal and distal end portions and being arranged coaxially within the elongated outer tubular member so as to form an annular gas flow passage therebetween, wherein a distal end portion of the trocar assembly defines an annular nozzle arrangement including an array of radially outwardly extending triangular jets arranged to direct humidified insufflation gas flowing through the annular gas flow passage into a patient's body cavity, wherein a base of each triangular jet extends over an arcuate section of the annular gas flow passage that is defined between the elongated inner tubular member and the elongated outer tubular member;
 c) a supply conduit for delivering the humidified insufflation gas to the annular gas flow passage; and
 d) a pressure source communicating with the supply conduit for regulating a supply of the humidified insufflation gas to the annular gas flow passage based on body cavity pressure sensed by a pressure sensor.

* * * * *